United States Patent
Daly

(10) Patent No.: US 8,697,451 B2
(45) Date of Patent: Apr. 15, 2014

(54) SULFUR BREAKTHROUGH DETECTION ASSEMBLY FOR USE IN A FUEL UTILIZATION SYSTEM AND SULFUR BREAKTHROUGH DETECTION METHOD

(75) Inventor: Joseph M. Daly, Bethel, CT (US)

(73) Assignee: FuelCell Energy, Inc., Danbury, CT (US)

( * ) Notice: Subject to any disclaimer, the term of this patent is extended or adjusted under 35 U.S.C. 154(b) by 476 days.

(21) Appl. No.: 12/951,679

(22) Filed: Nov. 22, 2010

(65) Prior Publication Data

US 2012/0129267 A1     May 24, 2012

(51) Int. Cl.
| | |
|---|---|
| G01N 25/32 | (2006.01) |
| G01N 25/36 | (2006.01) |
| G01N 33/22 | (2006.01) |
| G01N 31/10 | (2006.01) |
| B01J 8/06 | (2006.01) |
| H01M 8/22 | (2006.01) |

(52) U.S. Cl.
USPC .............. 436/119; 422/62; 422/105; 422/108; 422/109; 422/129; 422/625; 422/626; 422/629; 429/420; 429/425; 429/427; 429/428; 429/505; 436/37; 436/120; 436/121; 436/147; 436/155; 436/159; 436/181

(58) Field of Classification Search
USPC .......... 422/62, 105, 108–109, 129, 625–626, 422/629; 429/420, 425, 427–428, 505; 436/37, 119–121, 147, 155, 159, 181
See application file for complete search history.

(56) References Cited

U.S. PATENT DOCUMENTS

| | | | | |
|---|---|---|---|---|
| 3,649,202 A | * | 3/1972 | Bajek et al. | 422/62 |
| 3,838,994 A | * | 10/1974 | Aldridge | 48/215 |
| 3,943,226 A | * | 3/1976 | Difford | 423/230 |
| 4,034,061 A | * | 7/1977 | McArthur | 423/213.5 |
| 4,460,704 A | * | 7/1984 | Twigg | 502/302 |

(Continued)

FOREIGN PATENT DOCUMENTS

| | | |
|---|---|---|
| AT | 323330 T | 4/2006 |
| CA | 2458336 A1 | 3/2003 |

(Continued)

OTHER PUBLICATIONS

Loffler, D. G. et al, Journal of Power Sources 2003, 117, 84-91.*

(Continued)

*Primary Examiner* — Arlen Soderquist
(74) *Attorney, Agent, or Firm* — Cowan, Liebowitz & Latman, P.C.

(57) ABSTRACT

A sulfur breakthrough monitoring assembly for use in a fuel utilization system for detecting sulfur-containing compounds in desulfurized fuel, said monitoring assembly comprising: a heater for heating desulfurized fuel to a predetermined temperature, the predetermined temperature being between 450° C. and 600° C., a sulfur breakthrough detector adapted to receive heated fuel from the heater and including at least a reforming catalyst bed for reforming the heated fuel and a plurality of temperature sensors including a first temperature sensor for sensing temperature of the heated fuel before the fuel is conveyed through the reforming catalyst bed and a second temperature sensor for sensing temperature in the reforming catalyst bed, and a controller for determining whether concentration of the sulfur-containing compounds in the fuel exceeds a first predetermined concentration based on temperature outputs from the first and second temperature sensors.

30 Claims, 11 Drawing Sheets

(56) References Cited

U.S. PATENT DOCUMENTS

| | | | |
|---|---|---|---|
| 4,522,894 A * | 6/1985 | Hwang et al. | 429/425 |
| 4,891,464 A * | 1/1990 | Staggs | 585/440 |
| 5,120,511 A * | 6/1992 | Luft | 422/86 |
| 5,302,470 A | 4/1994 | Okada et al. | |
| 5,308,456 A * | 5/1994 | Kunz et al. | 429/410 |
| 5,389,342 A * | 2/1995 | Savage et al. | 422/109 |
| 5,531,424 A * | 7/1996 | Whipp | 266/156 |
| 5,925,476 A * | 7/1999 | Kawatsu | 429/424 |
| 6,221,117 B1 * | 4/2001 | Edlund et al. | 48/76 |
| 6,641,625 B1 * | 11/2003 | Clawson et al. | 48/127.9 |
| 6,641,795 B2 * | 11/2003 | Abe | 423/648.1 |
| 6,673,619 B2 * | 1/2004 | Sawada | 436/37 |
| 6,730,271 B2 * | 5/2004 | Hirata | 422/211 |
| 6,733,552 B1 * | 5/2004 | Taguchi et al. | 48/127.9 |
| 6,803,236 B2 * | 10/2004 | Bailey et al. | 436/37 |
| 6,969,505 B2 * | 11/2005 | Tonkovich et al. | 423/648.1 |
| 7,033,687 B2 * | 4/2006 | Ueda et al. | 429/412 |
| 7,063,732 B2 | 6/2006 | Katikaneni et al. | |
| 7,066,973 B1 * | 6/2006 | Bentley et al. | 48/197 R |
| 7,195,657 B2 * | 3/2007 | Ukai et al. | 48/61 |
| 7,267,991 B2 * | 9/2007 | Ceccarini et al. | 436/119 |
| 7,416,572 B2 * | 8/2008 | Wakao et al. | 48/198.7 |
| 7,449,167 B2 * | 11/2008 | Garg et al. | 423/654 |
| 7,452,391 B2 * | 11/2008 | Russell et al. | 48/195 |
| 7,455,923 B2 * | 11/2008 | Katikaneni et al. | 429/411 |
| 7,568,337 B2 * | 8/2009 | Uchida et al. | 60/276 |
| 7,758,984 B2 * | 7/2010 | Kim et al. | 429/420 |
| 7,763,087 B2 * | 7/2010 | Hajiaghajani et al. | 48/197 R |
| 8,080,426 B1 * | 12/2011 | Moore et al. | 436/120 |
| 2002/0031458 A1 * | 3/2002 | Hirata | 422/189 |
| 2002/0081253 A1 * | 6/2002 | Abe | 422/211 |
| 2002/0165417 A1 * | 11/2002 | Numaguchi et al. | 585/310 |
| 2002/0187890 A1 * | 12/2002 | Naka et al. | 502/38 |
| 2002/0197721 A1 * | 12/2002 | Kinugawa et al. | 436/37 |
| 2003/0032188 A1 * | 2/2003 | Bailey et al. | 436/37 |
| 2003/0039299 A1 * | 2/2003 | Horovitz et al. | 374/141 |
| 2003/0134425 A1 * | 7/2003 | Ceccarini et al. | 436/119 |
| 2004/0131540 A1 * | 7/2004 | Fujii et al. | 423/650 |
| 2004/0180247 A1 * | 9/2004 | Higashiyama et al. | 429/19 |
| 2004/0213734 A1 | 10/2004 | Bischoff | |
| 2004/0226218 A1 * | 11/2004 | Izawa et al. | 48/127.9 |
| 2005/0158594 A1 * | 7/2005 | Ahmed | 429/19 |
| 2005/0252083 A1 | 11/2005 | Kitagawa et al. | |
| 2006/0013759 A1 * | 1/2006 | Jiang et al. | 423/648.1 |
| 2006/0083956 A1 * | 4/2006 | Ukai et al. | 429/12 |
| 2006/0090398 A1 * | 5/2006 | Katikaneni et al. | 48/127.9 |
| 2006/0096175 A1 * | 5/2006 | Russell et al. | 48/127.5 |
| 2006/0177372 A1 * | 8/2006 | Doshi | 423/652 |
| 2006/0269804 A1 * | 11/2006 | Nakamura et al. | 429/22 |
| 2007/0010020 A1 * | 1/2007 | Elfvik et al. | 436/37 |
| 2007/0036713 A1 * | 2/2007 | Kobayashi et al. | 423/652 |
| 2007/0167323 A1 * | 7/2007 | Kobayashi | 502/341 |
| 2008/0101434 A1 * | 5/2008 | Horovitz et al. | 374/29 |
| 2008/0118794 A1 * | 5/2008 | Lee et al. | 429/17 |
| 2008/0139857 A1 * | 6/2008 | Henn et al. | 585/310 |
| 2008/0160367 A1 * | 7/2008 | Masui et al. | 429/20 |
| 2008/0187797 A1 * | 8/2008 | Edlund | 429/17 |
| 2009/0013600 A1 * | 1/2009 | Drnevich et al. | 48/127.7 |
| 2009/0029208 A1 | 1/2009 | Katikaneni et al. | |
| 2009/0061265 A1 * | 3/2009 | Lee et al. | 429/17 |
| 2009/0317671 A1 * | 12/2009 | Ukai et al. | 429/19 |
| 2010/0062295 A1 * | 3/2010 | Heo et al. | 429/19 |
| 2010/0068573 A1 * | 3/2010 | Tamura et al. | 429/19 |
| 2010/0120162 A1 * | 5/2010 | Stich | 436/119 |
| 2010/0183928 A1 * | 7/2010 | Fujihara et al. | 429/423 |
| 2010/0273069 A1 * | 10/2010 | Crumm et al. | 429/410 |
| 2010/0279185 A1 * | 11/2010 | Hatada | 429/425 |
| 2011/0027676 A1 * | 2/2011 | Hatada | 429/425 |
| 2011/0039174 A1 * | 2/2011 | Hatada | 429/425 |
| 2011/0039175 A1 * | 2/2011 | Yokoyama et al. | 429/425 |
| 2012/0015259 A1 * | 1/2012 | Budge | 429/410 |

FOREIGN PATENT DOCUMENTS

| | | |
|---|---|---|
| DE | 10141355 A1 | 3/2003 |
| ES | 2259732 T3 | 10/2006 |
| JP | 11-045731 A | 2/1999 |
| JP | 11-195424 A | 7/1999 |
| JP | 2000-233901 A | 8/2000 |
| JP | 2009-121296 A | 6/2009 |

OTHER PUBLICATIONS

Lampert, J., Journal of Power Sources 2004, 131, 27-34.*
Daly, J. et al, Journal of Power Sources 2007, 173, 925-934.*
Smith, T. R. et al, Applied Catalysis A: General 2009, 354, 1-7.*

* cited by examiner

SULFUR BREAKTHROUGH DETECTION ASSEMBLY FOR USE IN A FUEL UTILIZATION SYSTEM AND SULFUR BREAKTHROUGH DETECTION METHOD

This invention relates to fuel cells and, in particular, to detection of sulfur breakthrough in a desulfurizer assembly used with such fuel cells.

A fuel cell is a device which directly converts chemical energy stored in hydrocarbon fuel into electrical energy by means of an electrochemical reaction. Generally, a fuel cell comprises an anode and a cathode separated by an electrolyte, which serves to conduct electrically charged ions. Molten carbonate fuel cells operate by passing a reactant fuel gas through the anode, while oxidizing gas is passed through the cathode. In order to produce a useful power level, a number of individual fuel cells are stacked in series with an electrically conductive separator plate between each cell.

Current fuel cell technology requires clean fuel gas composed of hydrogen or a mixture of hydrogen, methane, carbon dioxide and carbon monoxide, which can be generated from hydrocarbon-containing feedstocks such as natural gas, propane, anaerobic digester gas, petroleum-based liquids or coal through a reforming process. Most hydrocarbon-containing feedstocks contain sulfur, which causes reforming and anode catalyst poisoning and is known to significantly diminish the performance of fuel cell anodes and reforming catalysts. Therefore, prior to the reforming process, sulfur and sulfur-containing compounds have to be removed from the fuel gas to a part per billion level before the fuel gas enters the fuel cell.

The present state of the art employs a fuel processing assembly, such as a desulfurizer assembly, that includes at least one adsorption or absorption bed for removal of sulfur-containing compounds from the fuel gas before passing the fuel gas to the fuel cell anode. An example of such a fuel processing assembly is disclosed in U.S. Pat. No. 7,063,732, which is assigned to the same assignee herein. The '732 patent discloses a fuel processing system for processing fuel for a fuel cell including a first adsorbent bed for adsorption of inorganic sulfur-containing compounds and high molecular weight organic sulfur-containing compounds and a second adsorbent bed for adsorption of low molecular weight organic sulfur-containing compounds, wherein the adsorbent beds are arranged such that the fuel to be processed passes through one of the adsorbent beds and thereafter through the other of the adsorbent beds. The '732 patent also discloses a lead-lag desulfurizer system for operation of the sulfur adsorbent system, which provides for optimal use of two or more desulfurizers by using a first desulfurizer as a lead desulfurizer and a second desulfurizer as a lag desulfurizer and redirecting fuel so as to use the second desulfurizer as the lead desulfurizer and the first desulfurizer as a lag desulfurizer when the first desulfurizer is exhausted and replenished with fresh adsorbent or regenerated. In this manner, the lag desulfurizer contains the fresher adsorbent and acts as the polishing desulfurizer, preventing damage to the fuel cell even if the lead desulfurizer has broken through. The lead-lag system of the '732 patent also allows the lead desulfurizer to be regenerated or replenished after it is exhausted, while operating on only the lag desulfurizer so as to achieve continuous desulfurizing of the fuel during replenishment of the lead desulfurizer. The disclosure of the '732 patent is incorporated herein by reference.

The adsorbent capacity and performance of the adsorbent bed used in the fuel processing system declines with operating time as the adsorbent bed becomes more saturated with sulfur-containing compounds. As a result, sulfur breakthrough occurs when the adsorbent bed becomes saturated and unable to decrease the concentration of the sulfur-containing compounds in the fuel to a desired level, normally expressed in parts per billion by volume (ppbv), and the amount of sulfur-containing compounds passing through the bed without being adsorbed, i.e. sulfur breakthrough concentration, increases as the saturation level of the sulfur-containing compounds in the bed is achieved. When a predetermined sulfur breakthrough concentration in the processed fuel is reached, the adsorbent bed has to be replaced or regenerated to avoid sulfur poisoning of the fuel cell system components. Due to variable concentrations of sulfur-containing compounds in the fuel gas and other changes in the fuel gas, such changes in hydrocarbon content and water content, the time when the predetermined level of sulfur breakthrough is reached can be highly variable. Therefore in order to ensure timely replacement or regeneration of the adsorbent bed, monitoring of the sulfur breakthrough concentration in the processed fuel is required.

Presently, the monitoring of the sulfur breakthrough concentration is usually accomplished by intermittently analyzing samples of processed fuel gas leaving the fuel processing assembly using techniques that are not practically applied in the field and are therefore performed in an analytical laboratory. Commonly used techniques for analyzing the sulfur concentration in the processed fuel include Gas Chromatography (GC) in conjunction with Sulfur Chemiluminescence Detection (GC-SCD) or Flame Photometric Detection (GC-FPD) techniques, as well as lead-acetate sulfur technique. However, these conventional techniques are expensive, thus substantially increasing the fuel processing costs and the operating costs of the fuel cell system. These techniques also require sampling of the processed fuel and transportation of the sample to the analytical laboratory, therefore requiring additional personnel and additional analytical equipment for sample collection, transportation from the field to a laboratory and performing the analysis of the processed fuel samples. As a result, the conventional methods cannot be integrated with the fuel cell processing assembly so as to continuously monitor the breakthrough sulfur concentration online.

Detector tubes may also be applied in the field to determine the concentration of specific sulfur compounds in the processed fuel. In general, the detector tubes function by a color change of a powder encased in a glass ampoule upon passing a predetermined volume of the process gas through the ampoule. The use of detector tubes requires personnel to travel to the site to perform the test. Detector tubes are also limited by interferences from other compounds in the fuel gas, are capable of detecting only one type of sulfur compound per type of detector tube, and have minimum detection levels that are typically too high to protect the fuel cell or other fuel processing components in the fuel cell fuel processing equipment.

An on-line sulfur breakthrough monitoring assembly and a sulfur breakthrough detection method have also been developed and are described in U.S. patent application Ser. No. 11/782,989, assigned to the same assignee herein. The monitoring assembly described in the '989 application uses indicator material which has one or more physical properties, such as color, that change when the indicator material is exposed to sulfur-containing compounds in fuel. The indicator material is disposed in a housing which can be placed on-line so that fuel output from a desulfurizer is passed through the indicator material, and a sensor is used to sense a change in one or more physical properties of the indicator material. The monitoring assembly of the '989 application is capable of continuously monitoring for sulfur-breakthrough concentration in the fuel and can be easily integrated with the fuel processing system.

The object of the present invention is to provide another sulfur breakthrough detection assembly which can be integrated with the fuel cell system and the fuel processing system, and which can continuously and accurately monitor for low level (parts per billion) sulfur breakthrough in the fuel.

It is a further object of the present invention to provide a sulfur breakthrough detection assembly which is highly sensitive and which can detect the parts per billion breakthrough of any sulfur species based on reforming catalyst deactivation by sulfur poisoning.

SUMMARY OF THE INVENTION

The above and other objectives are realized in a sulfur breakthrough monitoring assembly for use in a fuel utilization system for detecting sulfur-containing compounds in desulfurized fuel, said monitoring assembly comprising: a heater for heating the desulfurized fuel which has been humidified to a predetermined temperature, the predetermined temperature being between 450° C. and 600° C., a sulfur breakthrough detector adapted to receive heated humidified fuel from the heater and including at least a reforming catalyst bed for reforming the heated fuel and a plurality of temperature sensors including a first temperature sensor for sensing temperature of the heated fuel before the fuel is conveyed through the reforming catalyst bed and a second temperature sensor for sensing temperature in the reforming catalyst bed, and a controller for determining whether concentration of the sulfur-containing compounds in the fuel exceeds a first predetermined concentration based on temperature outputs from the first and second temperature sensors. In some embodiments, the monitoring assembly further includes a water supply for supplying purified water to the heater which heats the purified water and the desulfurized fuel to a predetermined temperature, a first flow control unit for controlling the flow of purified water to the heater and a second flow control unit for controlling the flow of desulfurized fuel entering the monitoring assembly. The controller receives temperature outputs from the first and second temperature sensors, determines the difference between these temperature outputs and determines that the concentration of the sulfur-containing compounds in the fuel exceeds the first predetermined concentration if the difference between outputs of the first and second temperature sensors decreases at a first predetermined rate. When the controller determines that the concentration of the sulfur-containing compounds in the fuel exceeds the first predetermined concentration, the controller activates an alarm and/or controls the fuel utilization system to perform one or more actions, which include controlling the flow of fuel to reduce or inhibit the fuel flow to one or more system components or to the system, controlling the desulfurizer assembly to redirect the flow of fuel to another desulfurizer and/or controlling the system to switch to another fuel supply.

In certain embodiments, the controller also determines whether the concentration of the sulfur-containing compounds exceeds a second predetermined concentration based on whether the difference between temperature outputs from the first and second temperature sensors decreases at a second predetermined rate that is greater than the first predetermined rate. If the controller determines that the concentration of sulfur-containing compounds exceeds the second predetermined concentration, then the controller activates an escalated alarm and performs one or more predetermined escalated actions.

In certain embodiments, the controller also controls the flow of fuel to the sulfur breakthrough detector so that the space velocity of the fuel through the reforming catalyst is between 30,000/hr and 120,000/hr and the superficial velocity of the fuel through the reforming catalyst is between 7 and 60 cm/sec.

A method of monitoring sulfur breakthrough in a fuel utilization system and detecting sulfur-containing compounds in the fuel is also described.

BRIEF DESCRIPTION OF THE DRAWINGS

The above and other features and aspects of the present invention will become more apparent upon reading the following detailed description in conjunction with the accompanying drawings, in which.

DETAILED DESCRIPTION

Figure 1:
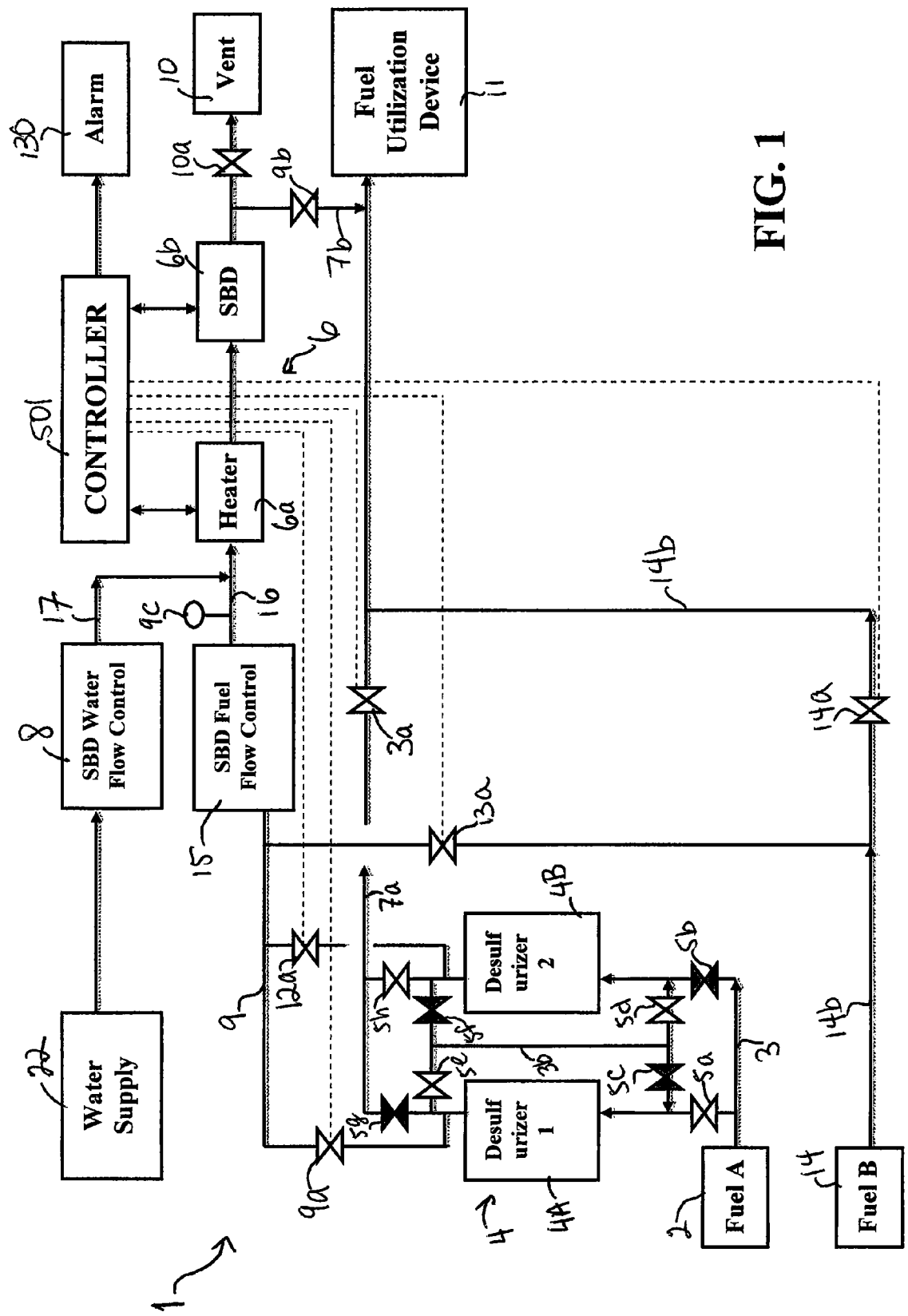
FIG. 1 shows a sulfur breakthrough monitoring assembly being used in a fuel utilization system.

FIG. 1 illustrates a fuel utilization system 1 including a desulfurizing system 4, including desulfurizers 4A and 4B, for removing sulfur-containing compounds from Fuel A received from a fuel supply 2 and a fuel utilization device 11 which receives desulfurized fuel from the desulfurizing system 4 and utilizes or processes the Fuel A. The fuel utilization device 11 may or may not also utilize other fuels, such as Fuel B, and is not limited to any specific number of fuels or number of fuel supplies from which the fuel utilization device 11 may receive fuel. The fuel utilization device 11 is any device, system or assembly that uses or processes fuel, and requires or prefers fuel that is free or substantially free of sulfur-containing compounds. Fuel utilization devices may include fuel cell systems, fuel reforming systems, power plants, such as fuel cell power plants, any devices operating on fuel or generating electrical or any other type of energy from fuel, and any other processing or utilization devices. As shown, the fuel utilization system 1 is supplied with Fuel A from the fuel supply 2 connected to the desulfurizing system 4 by a connecting line 3, and a first flow control member 3a, such as a flow control valve, is used to control the flow of fuel from the fuel supply 2 through the desulfurizing system 4 to the fuel utilization device 11. The construction and type of the desulfurizing system 4 may vary depending on the requirements of the fuel utilization device 11. In certain embodiments, the desulfurizing system 4 includes one or more desulfurizers 4A and 4B, each of which includes one or more adsorbent and/or absorbent beds comprising adsorbent and/or absorbent materials. The adsorbent and/or absorbent beds of the desulfurizers of the desulfurizing system 4 remove sulfur-containing compounds present in the fuel being passed therethrough by chemical or physical adsorption or by absorption. In some embodiments, the desulfurizing system 4 includes a plurality of desulfurizers disposed at least in parallel so fuel is desulfurized by at least one of the desulfurizers while one or more other desulfurizers are in standby. In such desulfurizing systems, the fuel flow may be switched from the operating desulfurizer(s) to one or more of the other desulfurizers when the amount of sulfur breakthrough in desulfurized fuel is greater than an acceptable amount. In some embodiments, the desulfurization system 4 includes a plurality of desulfurizers disposed in series and/or in parallel, so that one of the desulfurizers 4A operates as a lead desulfurizer and the other desulfurizer 4B operates as a lag desulfurizer. Such a desulfurizing system 4 is shown in the illustrative embodiment of FIG. 1. As shown in FIG. 1, flow control members, such as valves 5a-h, are used to control the flow of fuel through the desulfurizers 4A and 4B. For example, as shown in FIG. 1, the valves 5a, 5d, 5e and 5h are open and valves 5b, 5c, 5f and 5g are closed so that the Fuel A is first conveyed to the first desulfurizer 4A and thereafter to the second desulfurizer 4B. When the capacity of the first desulfurizer 4A is reduced beyond a predetermined level, the fuel is redirected through the second desulfurizer 4B, which becomes the lead desulfurizer while the first desulfurizer is replenished with fresh adsorbent or regenerated and becomes the lag desulfurizer. In this case, the valves 5a, 5d, 5e and 5h would be closed and valves 5b, 5c, 5f and 5g would be opened. In addition, either desulfurizer A or desulfurizer B may be isolated from the Fuel A while Fuel A continues to flow though the other desulfurizer so as to allow the isolated desulfurizer to be regenerated while the fuel is being directed through the other desulfurizer. Desulfurized fuel output from the first desulfurizer 4A is then passed through a connecting line 3b to a polishing or lag desulfurizer 4B and then on to connecting line 7a to the fuel utilization device 11.

As shown in FIG. 1, a sulfur breakthrough monitoring assembly 6 is used with the fuel utilization system 11 for detecting and monitoring breakthrough concentration of sulfur-containing compounds downstream from the first desulfurizer 4A and/or downstream of the second desulfurizer 4B. The sulfur breakthrough monitoring assembly 6 of this embodiment can be used with, and incorporated into, any fuel utilization system that requires monitoring of sulfur breakthrough concentrations in the fuel. As shown, the sulfur breakthrough monitoring assembly 6 receives at least a portion of the desulfurized fuel output from the desulfurizer 4A and/or 4B through a connecting line 9 and monitors the rate of sulfur breakthrough increase in the fuel based on temperature variations in the monitoring assembly 6 as described in more detail below. The monitoring assembly 6 also can activate one or more alarms or signals based on the monitoring of the rate of sulfur breakthrough in the fuel, and these alarms or signals can escalate as the rate of sulfur breakthrough in the fuel increases. The alarms or signals activated by the monitoring assembly 6 control the system to perform one or more predetermined actions if the monitoring assembly 6, based on the monitoring of the rate or concentration of sulfur breakthrough in the fuel, determines that the sulfur breakthrough in the fuel is increasing at a rate that is higher than a predetermined acceptable rate or if the concentration of sulfur-containing compounds is higher than a predetermined acceptable concentration.

As shown in FIG. 1, a portion of the fuel output from the desulfurizer 4A is supplied to the monitoring assembly 6 via the connecting line 9. As shown, the connecting line 9 includes a flow control member 9a, and may also include an optional flow transmitter or flow indicator 9c. The flow control member 9a controls the flow rate of desulfurized Fuel A supplied to the monitoring assembly 6 and in this illustrative embodiment, controls the amount of the desulfurized fuel so that the flow rate of the fuel supplied to the monitoring assembly is between 0.5 and 2 slpm. Other fuels may also be selected by the controller for sulfur breakthrough detection, by actuation of flow control members 12a or 13a, to select, respectively, Fuel A exiting Lag Desulfurization Vessel 4B, or Fuel B, or another fuel. In the present illustrative embodiment, the sulfur breakthrough monitoring assembly 6 also includes a water flow control assembly 8 for controlling the flow of water, or deionized water, from a water supply 22 to a heater 6a after combining the water with the selected fuel. In the present illustrative embodiment, the water flow control assembly 8 and a fuel flow assembly 15 control the flow of water and selected fuel, respective so that the resulting humidified fuel has a steam to carbon ratio (S/C) of 1.3-3.0. The method of controlling the fuel flow may be a forward pressure regulator followed by a back pressure regulator with an orifice or valve in between, to provide a fixed pressure drop across a fixed orifice, thereby controlling the flow of fuel in line 16. There are many other acceptable means of controlling the fuel flow, such as a thermal mass flow controller. Likewise, the method of controlling the water flow may be a forward pressure regulator followed by a back pressure regulator with an orifice or valve in between, to provide a fixed pressure drop across a fixed orifice, thereby controlling the flow of water in line 17. There are also many other acceptable means of controlling the water flow, such as a micro metering pump, or a humidifier in which the fuel is bubbled through a heated column of water to provide the desired dew point, or steam to carbon ratio, at the exit.

Figure 2:
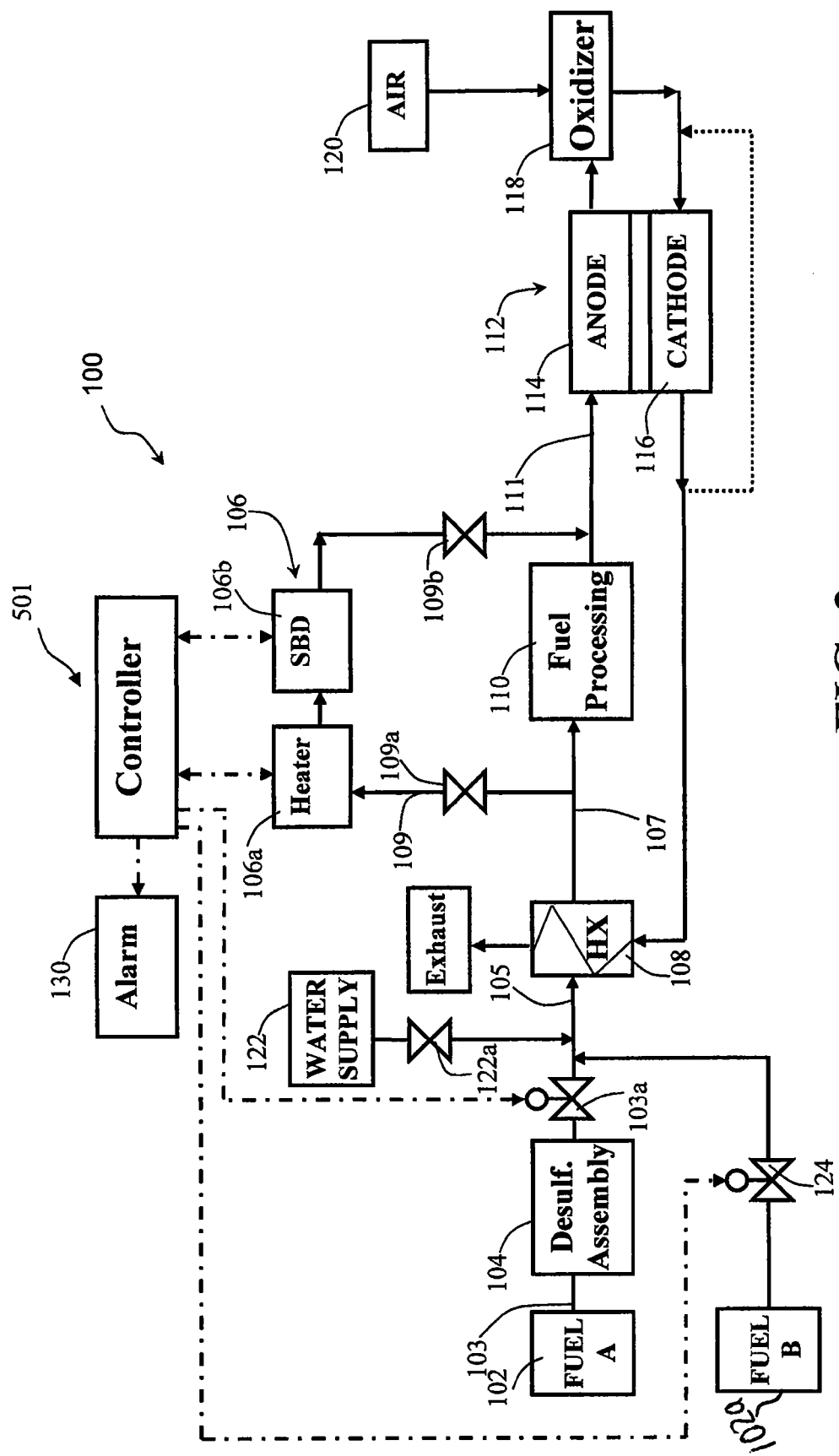
FIG. 2 shows a fuel cell system employing a sulfur breakthrough monitoring assembly for detecting breakthrough concentration of sulfur downstream of a desulfurizer assembly and downstream of the flow metering of the input purified water and desulfurized fuel, such that the ratio of fuel and water are predetermined and not controlled by the monitoring assembly.

In some embodiments, the fuel utilization system includes a humidification assembly that humidifies the desulfurized fuel before it is supplied to the monitoring assembly 6, and in such embodiments the water control assembly 8 may be omitted so that humidified desulfurized fuel is provided directly to the monitoring assembly. In such embodiments, a fuel control member may be used for controlling the flow rate of desulfurized humidified fuel to the monitoring assembly. An example of this embodiment is shown in FIG. 2.

As shown in FIG. 1, the sulfur breakthrough monitoring assembly 6 comprises a heater 6a, which heats the fuel to a predetermined temperature, and a sulfur breakthrough detector 6b, which comprises at least reforming catalyst. As discussed in more detail below, the sulfur breakthrough monitoring assembly 6 includes a plurality of temperature sensors, or thermocouples, which sense or detect the temperatures in the heater 6a and at predetermined portions of the sulfur breakthrough detector 6b.

Figure 3A:
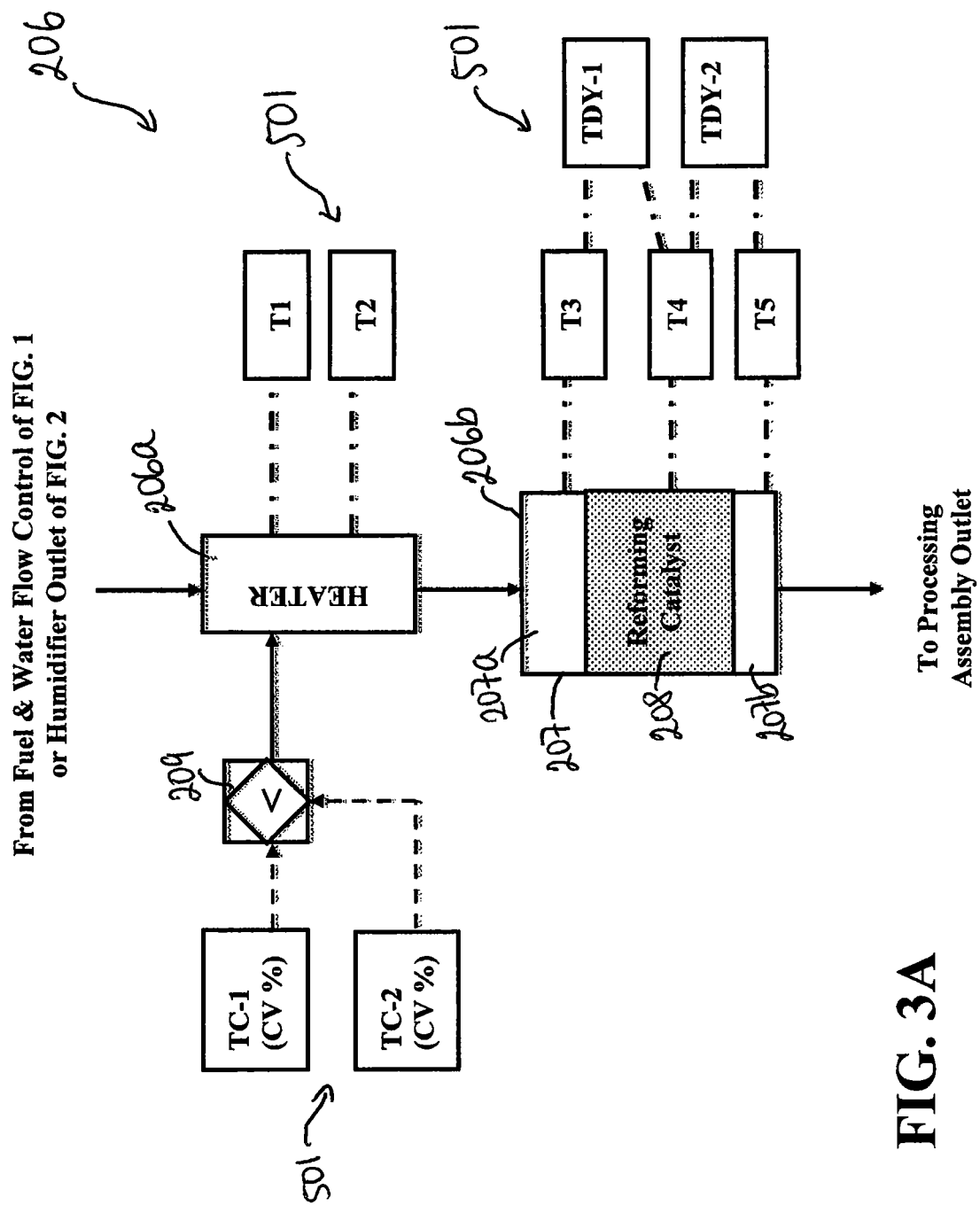
FIG. 3A shows a schematic view of one embodiment of the sulfur breakthrough monitoring assembly of FIGS. 1 and 2.
Figure 3B:
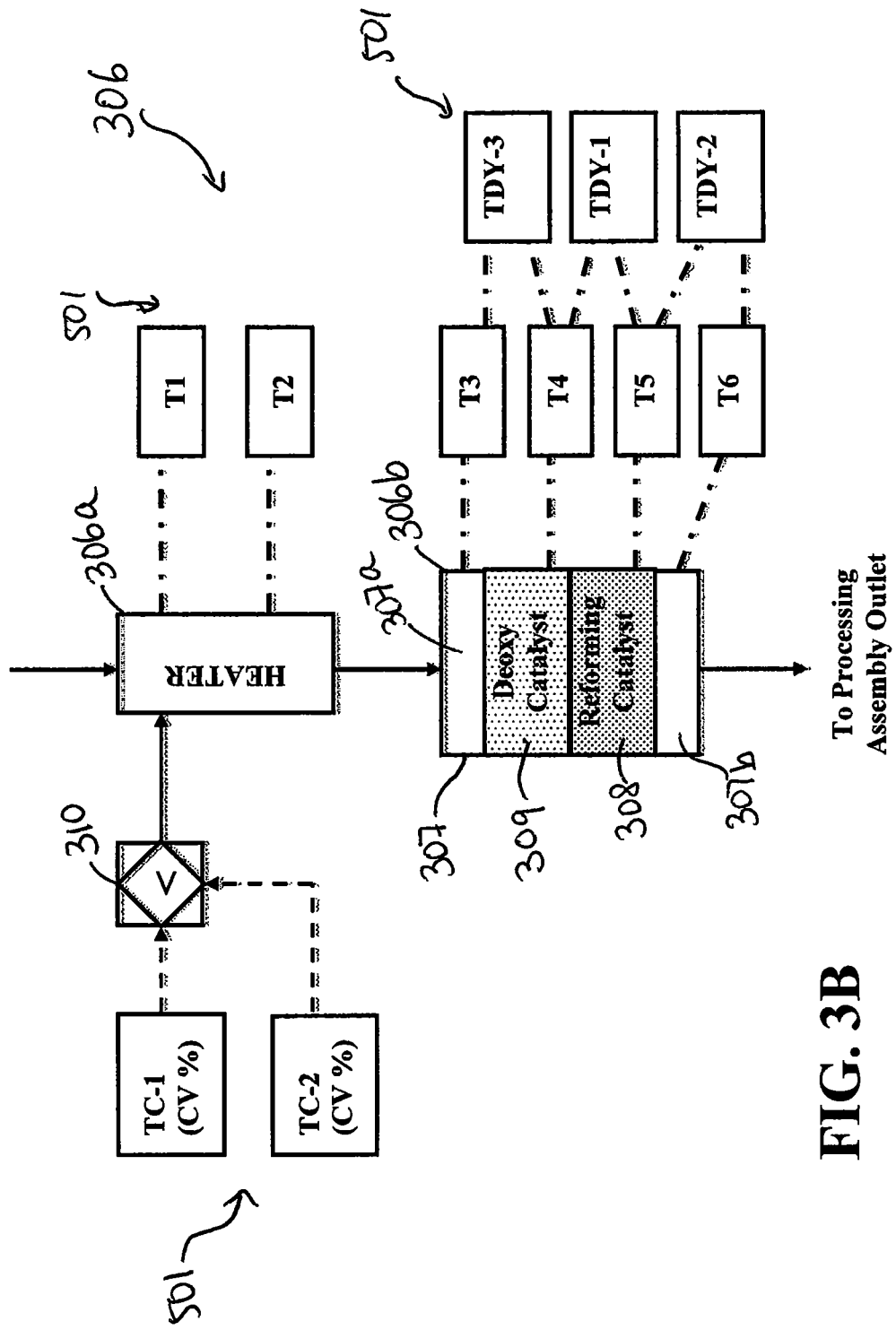
FIG. 3B shows a schematic view of another embodiment of the sulfur breakthrough monitoring assembly of FIGS. 1 and 2.

As shown, the sulfur breakthrough monitoring assembly 6 also includes a controller assembly 501 that includes at least one controller for controlling at least the heater 6a and the sulfur breakthrough detector 6b based on the temperatures sensed by the temperature sensors. As also described in more detail below, changes in temperatures sensed by the temperature sensors are monitored and based on the changes in the temperatures detected by the temperature sensors, the controller assembly 501 determines whether or not sulfur breakthrough has occurred and whether or not the sulfur breakthrough in the fuel is increasing at a higher than acceptable rate. In some embodiments, the controller assembly 501 also determines, based on the changes in the detected temperatures, whether or not the fuel flow through the monitoring assembly 6 is sufficient and whether or not the fuel flow is constant. Based on these determinations, the controller assembly 501 activates one or more alarms or signals, which escalate as the rate and amount of sulfur breakthrough in the fuel increases, and which control the fuel utilization system 1 to perform one or more predetermined actions. These predetermined actions include an activation of an alarm 130, such as a pager alarm to an operator and/or an alarm indicating a need for replacement or regeneration of at least one desulfurizer 4A or 4B of the desulfurizing system 4, controlling the desulfurizing system to inhibit the flow of fuel through an operating desulfurizer and to redirect fuel flow through another desulfurizer, switching to another fuel, e.g. Fuel B, and controlling the flow of desulfurized fuel to the fuel utilization device so as to minimize or altogether inhibit the flow of fuel to the fuel utilization device. More detailed constructions of the sulfur breakthrough monitoring assemblies 6 that can be used together with the fuel utilization system 1 of FIG. 1 are shown in FIGS. 3A and 3B and are described in more detail herein below.

As shown in FIG. 1, fuel output from the sulfur breakthrough detector 6 is conveyed to a vent 10 through a vent flow controller 10a and/or can be combined with the desulfurized fuel flowing through the connecting line 7b to the fuel utilization device 11. A flow control member 9b is used for controlling the flow of fuel output from the monitoring assembly 6 to the connecting line 7b.

As discussed above, the fuel utilization device 11 may receive another fuel from another fuel supply instead of Fuel A or in addition to Fuel A. As shown in FIG. 1, Fuel B, which can be the same or different fuel than Fuel A, is supplied from another fuel supply 14 to the fuel utilization device via a line 14b. The flow of Fuel B to the fuel utilization device 11 is controlled by a Fuel B controller 14a, such as a valve, and as discussed above, a portion of the Fuel B may be conveyed to the monitoring assembly 6 through the flow controller 13a. As shown in FIG. 1, the flow controllers 13a and 14a are controlled by the controller 501. In addition, the controller 501 may control the flow controllers 3a, 9a and 12a so as to control the flow of fuel A to the fuel utilization device and to the monitoring assembly 6.

FIG. 2 illustrates a fuel cell system 100 which includes a desulfurizer assembly 104 and a sulfur breakthrough monitoring assembly 106 for detecting and monitoring breakthrough concentration of sulfur downstream from the desulfurizer assembly 104. The fuel cell system 100 is supplied with fuel from a fuel supply 102 connected to the desulfurizer assembly 104 by a connecting line 103. A first flow control member 103a, such as a flow control valve, is used to control the flow of fuel from the fuel supply 102 through the desulfurizer assembly 104 to the fuel humidifier 108.

The desulfurizer assembly 104 includes one or more desulfurizers each of which includes one or more adsorbent and/or absorbent beds comprising adsorbent and/or absorbent materials. Sulfur-containing compounds present in the fuel being passed through the desulfurizer assembly 104 are removed from the fuel using the adsorbent and/or absorbent beds by chemical or physical adsorption or by absorption. Desulfurized fuel from the desulfurizer assembly 104 is thereafter passed through a connecting line 105 to a humidifier 108 where the fuel is humidified with water provided from a water supply 122. In the present illustrative embodiment, a water flow controller 122a and the fuel flow controller 103a control the ratio of fuel and water so that the humidifier 108 humidifies the fuel and such that the steam to carbon ratio (S/C) of the humidified fuel is 1.3 or greater, and preferably to S/C ratio of 1.5 to 3.0, which is suitable for use in a Direct Fuel Cell (DFC) power plant. Fuel and/or water flow metering devices may be used as the fuel flow controller 103a and/or the water flow controller 122a, respectively, for controlling the flow of fuel and water from the fuel supply 102 and water supply 122, respectively. In the humidifier 108, the fuel may also be heated by heat exchange using heat from cathode exhaust gas. The humidified fuel is then conveyed to a fuel processing assembly 110 by a connecting line 107. As shown, a portion of the fuel output from the humidifier 108 is conveyed from the connecting line 109 to the sulfur breakthrough monitoring assembly 106 via a flow control member 109a. The monitoring assembly 106 continuously monitors the desulfurized fuel for the presence of sulfur-containing compounds therein, i.e., sulfur breakthrough, and is disposed in parallel with the fuel processing assembly 110. The fuel conveyed through the monitoring assembly is then combined in a connecting line 111 with the other portion of the fuel which is processed by the fuel processing assembly 110 and output from the fuel processing assembly 110 to the connecting line 111. A flow control valve 109b is used to control the flow of fuel from the monitoring assembly 106 to the connecting line 111.

As shown in FIG. 2, the sulfur breakthrough monitoring assembly 106 comprises a heater 106a which heats the fuel to a predetermined temperature and a sulfur breakthrough detector 106b which comprises at least reforming catalyst. As discussed in more detail below, the sulfur breakthrough monitoring assembly 106 includes a plurality of temperature sensors, such as thermocouples, which sense or detect the temperatures in the heater 106a and at predetermined portions of the sulfur breakthrough detector 106b. The sulfur breakthrough monitoring assembly 106 also includes a controller assembly 501 that includes at least one controller for controlling at least the heater 106a and the sulfur breakthrough detector 106b based on the temperatures sensed by the temperature sensors. As also described in more detail below, changes in temperatures sensed by the temperature sensors are monitored and based on the changes in the temperatures detected by the temperature sensors, the controller assembly 501 determines whether or not sulfur breakthrough has occurred and whether the concentration of the sulfur breakthrough in the fuel is equal to or greater than a predetermined concentration. The predetermined concentration may be varied depending on the requirements of the system and in the illustrative embodiments described below, the predetermined concentration is 30 ppb or 200 ppb. The controller assembly 501 can also determine whether or not the sulfur breakthrough in the fuel is increasing at a high rate. In some embodiments, the controller assembly 501 also determines based on the changes in the detected temperatures whether or not the fuel flow through the monitoring assembly is sufficient and whether or not the fuel flow is constant. Based on these determinations, the controller assembly 501 activates one or more alarms in an escalating manner as the rate and amount of sulfur breakthrough in the fuel increases, which in some cases control the fuel cell system to perform at least one predetermined action. Predetermined actions include an activation of an alarm 130, such as a pager alarm to a system operator or an alarm indicating a need for replacement or regeneration of at least one desulfurizer of the desulfurizer assembly 104, controlling the desulfurizer to inhibit the flow of fuel through an operating desulfurizer and to redirect fuel flow through another desulfurizer, controlling the flow of desulfurized fuel to the fuel cell so as to minimize or inhibit the flow of fuel to the fuel cell, and switching over to an alternate fuel supply having its own independent desulfurization system, e.g. Fuel B. Constructions of the sulfur breakthrough monitoring assembly 106 are shown in FIGS. 3A and 3B and are described in more detail herein below.

In certain embodiments, the desulfurizer assembly 104 includes a plurality of desulfurizers, each of the desulfurizers including at least one desulfurizing bed, wherein the desulfurizers are coupled with one another so as to allow at least one of the desulfurizers to be operational while one or more of the other desulfurizers are in standby mode or are coupled so that the fuel passes in series through the first desulfurizer and then through the second desulfurizer. An example of such desulfurizer assembly, which includes a "lead lag" system, is discussed above and disclosed in commonly assigned U.S. Pat. No. 7,063,732, which is hereby incorporated by reference. As discussed in the '732 patent, the desulfurizer assembly in such embodiments includes one or more fuel flow control members (not shown for purpose of simplicity) to direct the flow of fuel through at least one of the desulfurizers. In such embodiments, when the controller assembly 501 determines, based on a predetermined temperature change sensed by the temperature sensors, that the concentration of sulfur breakthrough in the fuel is equal to or greater than the predetermined concentration, the controller assembly 501 controls the fuel flow control members of desulfurizer assembly 104 to inhibit or limit the flow of fuel through the operational desulfurizer and to direct the flow of fuel through at least one of the other desulfurizers on standby. For example, if the sulfur breakthrough detector of FIG. 1 is being used to detect the sulfur breakthrough in the lead bed and detects sulfur in the lead bed, or a higher than a predetermined concentration or rate of increase of sulfur in the lead bed, the controller may cause the fuel to bypass the lead bed and to be desulfurized by only the lag bed. Alternatively, if the sulfur breakthrough detector of FIG. 2 is being used to detect sulfur breakthrough in Fuel A and detects sulfur in fuel A, or a higher than a predetermined concentration or rate of increase of sulfur in Fuel A, the controller may control the system to switch to fuel B. The controller assembly 501 may also activate an alarm indicating a need for replacement or regeneration of the previously operational desulfurizer. In certain embodiments, the controller assembly 501 also controls the desulfurizer assembly 104 to automatically regenerate the previously operational desulfurizer when the fuel flow through the previously operational desulfurizer is inhibited or if the alarm indicating that the previously operational desulfurizer needs to be regenerated is activated.

As shown in FIG. 2, the fuel cell system 100 includes the fuel flow control member 103*a* for controlling the flow of desulfurized humidified Fuel A to the fuel processing assembly 110. In some illustrative embodiments, the controller assembly 501 controls the fuel flow control member 103*a* for Fuel A and a fuel flow control member 124 for Fuel B to control the flow rate of the fuels to the fuel processing assembly 110 and to the fuel cell 112. In such embodiments, when the controller assembly 501 determines, based on the changes in the temperatures sensed by the temperature sensors, that the concentration of sulfur breakthrough in whichever fuel is flowing to the fuel processing assembly 110 is equal to or greater than the predetermined amount, or that rate of sulfur breakthrough in the fuel increases at a rate that is greater than an acceptable rate, the controller assembly 501 controls the fuel flow control members 103*a* and 124 to inhibit or limit the flow of whichever fuel is presently flowing to the fuel processing assembly 110 so as to prevent poisoning of catalyst in the fuel processing assembly 110. In certain embodiments, the controller assembly 501 first activates an alarm state or a warning when the temperature change sensed by the sensors is greater than a threshold amount, and thereafter controls the fuel flow control members 103*a* and 124 to inhibit or limit the flow of the presently flowing fuel therethrough if it is determined that the concentration of the sulfur breakthrough in the presently flowing fuel is equal to or greater than the predetermined concentration and/or the sulfur breakthrough concentration is increasing at a higher than the acceptable rate. The controller assembly 501 may also control the flow of desulfurized humidified fuel to the monitoring assembly 106 by controlling the valve 109*a*.

As shown in FIG. 2, the system 100 also includes the fuel processing assembly 110 for further processing the fuel, a fuel cell 112, including an anode 114 and a cathode 116, and an oxidizer assembly 118. In the present illustrative embodiment, the fuel processing assembly 110 includes a pre-reforming assembly, including a reforming catalyst, for reforming at least a portion of the fuel so as to produce fuel suitable for use in the fuel cell 112. In some embodiments, the fuel processing assembly 110 includes a deoxidizing assembly, including a deoxidizing catalyst, for removing oxygen from the fuel. In the embodiments in which the fuel processing assembly includes the deoxidizing assembly and the pre-reforming assembly, the deoxidizing and pre-reforming assemblies are disposed so that the fuel is first passed through the deoxidizing assembly and thereafter through the pre-reforming assemblies so that oxygen is removed from the fuel prior to reforming the fuel. In this way, deactivation or damaging of the reforming catalyst is prevented.

Fuel processed in the fuel processing assembly 110 is thereafter conveyed via the connecting line 111 to the anode 114 of the fuel cell 112. As shown in FIG. 2, the output from the monitoring assembly 106 may also be conveyed to the connecting line 111 where it is combined with the output from the fuel processing assembly and both output portions are conveyed to the anode 114, where the fuel undergoes an electrochemical reaction with an oxidant gas flowing through the cathode 116 to produce electrical power. As also shown, spent fuel leaving the anode 114, i.e. anode exhaust, which includes unreacted fuel, is conveyed to the oxidizer 118 where it is combined with air from an air supply 120 and combusted or oxidized to produce oxidant gas suitable for use in the cathode 116. Spent oxidant gas leaving the cathode 116, in turn, may be passed to the humidifier 108 for heating desulfurized fuel and water and/or may be recycled back to the cathode 116.

FIGS. 3A and 3B show two embodiments of the sulfur breakthrough monitoring assembly which can be used in a fuel cell system as shown in FIG. 2 or in the fuel utilization system of FIG. 1. It is understood, however, that the sulfur breakthrough monitoring assemblies of FIGS. 3A and 3B can be used in any systems that require sulfur monitoring in fuel or other gases. The first embodiment of the sulfur breakthrough monitoring assembly 206 is shown in FIG. 3A and is suitable for monitoring sulfur breakthrough in fuel that has no or only a small amount of oxygen. As shown in FIG. 3A, the monitoring assembly 206 comprises a heater 206*a*, which receives desulfurized fuel from the connecting line 16 plus water from the connecting line 17 in the embodiment of FIG. 1, or humidified fuel from the connecting line 109 in the embodiment of FIG. 2, and heats the humidified fuel to a predetermined temperature. When the monitoring assembly 206 is used in the system shown in FIG. 1, the fuel in the connecting line 16 is humidified by being combined with the water from the water supply and conveyed through the line 17 via the water flow controller 8, as described above. In the present illustrative embodiment, the predetermined temperature to which the heater heats the fuel is between 450° C. and 600° C., with a preferred predetermined temperature being between 475° C. and 550° C. In the operation example described below, the predetermined temperature is 500° C. However, the predetermined temperature is dependent on the types of sulfur-containing compounds being monitored in the fuel and the desired minimum detection level, and thus may be different in other applications or embodiments. In particular, it has been found by applicants that elevated operating temperatures are required during operation of the sulfur breakthrough monitoring assembly in order to monitor certain types of sulfur-containing compounds, such as dimethyl sulfide. This is because the elevated temperatures are required for some sulfur-containing compounds to react with the catalyst in the sulfur breakthrough detector 206b so as to poison the catalyst rather than allowing those sulfur-containing compounds to simply pass through the catalyst. At the same time, the predetermined temperature should not be so high as to cause sintering of the catalyst in the sulfur breakthrough detector 206b. At the minimum, the fuel is heated to the predetermined temperature so that the monitoring assembly is able to detect the typical breakthrough sulfur species, for example: DMS (dimethyl sulfide), COS (carbonyl sulfide), EMS (ethyl methyl sulfide), THT (tetrahydrothiophene), CS2 (carbon disulfide) and H2S (hydrogen sulfide).

The heater 206a used in the monitoring assembly is a compact, low wattage heater. In the present illustrative embodiment, the heater includes a length of ⅜" tubing, which conveys the water and fuel (FIG. 1), or humidified fuel gas (FIG. 2), coiled around a cartridge heater. Fuel is conveyed through the tubing coil of the heater 206a and is heated by the heater to the predetermined temperature. The temperature in the heater 206a is measured using one or more temperature sensors. As shown in FIG. 3A, a first temperature sensor T1 and a second temperature sensor T2, both of which comprise thermocouples, are provided for sensing the temperature in the heater 206a. In the embodiment shown, two thermocouples T1 and T2 are provided for sensing the temperature of the heater as a safety measure in case one of the thermocouples fails. In such embodiments, temperature sensed by one of the thermocouples T1 and T2 is used for controlling the heating by the heater 206a, while the temperature sensed by the other thermocouple T1 or T2 is only used as a safety backup in case of thermocouple failure. In other embodiments, only one temperature sensor may be used for sensing the temperature in the heater 206a.

As shown in FIG. 3A, the monitoring assembly 206 further comprises a sulfur breakthrough detector (SBD) 206b, which receives fuel heated by the heater 206a and through which the heated fuel is conveyed. The sulfur breakthrough detector 206b comprises a housing 207 and a reforming catalyst bed 208 disposed in the housing 207. The dimensions of the housing 207 and the catalyst bed 208 may vary dependent on the amount of fuel flow to be passed through the monitoring assembly 206 and the sensitivity of the monitoring assembly 206. In the present illustrative embodiment, when the monitoring assembly is used with a fuel cell system of FIG. 2, about 6 slpm of humidified fuel is conveyed from the connecting line 107 to the sulfur breakthrough monitoring assembly, which comprises about 0.2% of the total fuel required for 300 kW net AC fuel cell operation. In the embodiment of FIG. 2, the humidified fuel is conveyed to the sulfur breakthrough monitoring assembly at lower flow rates when the fuel cell is producing less power and therefore the total fuel gas output from the humidifier is less. For example, the humidified fuel may be conveyed to the breakthrough monitoring assembly at a flow rate of 1.0 to 3.8 slpm, which is a portion of the fuel gas output from the humidifier at a flow rate of 500 to 1900 slpm. When the monitoring assembly is used with the fuel utilization system of FIG. 1, the (dry) fuel is conveyed to the monitoring assembly at a controlled flow rate of 0.5 to 2.0 slpm. In the embodiment of FIG. 1 the fuel flow rate and even the fuel flow type to the sulfur breakthrough monitoring assembly 6 is independent of the fuel flow to the fuel utilization device, with the fuel flow type being controlled by the selection valves 9a, 12a, and 13a, and the fuel flow rate being controlled by the fuel flow controller 15.

In this illustrative embodiment, the housing 207 of the sulfur breakthrough monitoring assembly 206 is a substantially cylindrical housing formed from metallic materials, such as stainless steel, and has a diameter of 1 inch (2.54 cm) and a height or length of 3 inches (7.62 cm). The housing 207 in this embodiment houses therein a reforming catalyst bed 208 that includes 5 grams of nickel-based reforming catalyst and has a depth of about 5 mm. The reforming catalyst bed is supported within the housing 207 by a screen about 1 inch (2.54 cm) away from the outlet end of the housing 207. The nickel-based indirect reforming catalyst suitable for use in the catalyst bed 208 of the sulfur breakthrough detector 206b is in the form of pellets or the like and in some embodiments comprises a small precious metal component, such as 0.1-1.0 weight % of rhodium, platinum, palladium or another precious metal. In some embodiments, the reforming catalyst used in the catalyst bed 208 may be reduced and stabilized, while in other embodiments the reforming catalyst in an oxidized state may be used in the catalyst bed 208 and thereafter reduced in-situ using hydrogen gas, blended with nitrogen, prior to exposing the catalyst to the humidified fuel. It is understood that the configuration and dimensions of the housing 207 and the catalyst bed 208 described above are illustrative and that other configurations and dimensions may be used.

As shown in FIG. 3A, temperatures within the sulfur breakthrough detector are sensed and monitored by a plurality of temperature sensors T3, T4 and T5, which can be in the form of thermocouples. A third temperature sensor, or thermocouple, T3 senses the temperature of the heated fuel flowing through an inlet portion 207a of the housing 207 and prior to entering the reforming catalyst bed 208. A fourth temperature sensor, or thermocouple, T4 senses the temperature in the reforming catalyst bed 208, and a fifth temperature sensor, or thermocouple, T5 senses the temperature of the fuel flowing through an outlet portion 207b of the housing 207 after the fuel has passed through the reforming catalyst bed 208. As described below, the temperatures sensed by the temperature sensors T3, T4 and T5 are used for monitoring sulfur breakthrough presence and amounts in the fuel and for determining whether the amount of sulfur breakthrough in the fuel is increasing at a high rate. As also described, the temperatures sensed by the temperature sensors T1 to T5 may also be used for controlling the heating of the heater and for determining whether the fuel flow rate through the sulfur breakthrough monitoring assembly is sufficient to maintain accurate and precise monitoring of the sulfur breakthrough.

During operation of the sulfur breakthrough monitoring assembly 206, desulfurized and humidified fuel portion is heated to a constant predetermined temperature by the heater 206a and thereafter guided through the sulfur breakthrough detector 206b. In the sulfur breakthrough detector 206b, the heated fuel is partially reformed by the reforming catalyst in the catalyst bed 208 before being output from the housing 207 of the sulfur breakthrough detector 206b. The temperature of the reforming catalyst bed 208 is dependent on the rate of the reforming process by which the fuel is reformed, which is directly related to the condition of the reforming catalyst in the catalyst bed 208. Sulfur-containing compounds, when present in the fuel flowing through the catalyst bed 208, poison the reforming catalyst thus causing the rate of fuel reforming to decrease. Since the reforming reaction is endothermic, the decrease in the rate of fuel reforming by the reforming catalyst causes the temperature in the catalyst bed 208 to rise as the amount of sulfur-containing compounds present in the fuel increases, thus indicating sulfur poisoning of the reforming catalyst in the catalyst bed 208.

During operation, the rate at which the temperature in the catalyst bed 208 increases is related to the amount or concentration of sulfur breakthrough present in the fuel. As a result, if the amount of sulfur-containing compounds in the fuel is relatively small, e.g., less than 30 ppb or less than 100 ppb, and relatively constant, then the temperature in the catalyst bed 208 will increase gradually and slowly at a rate that is smaller than a first predetermined rate. For example, a relatively small amount of sulfur breakthrough in the fuel, such as <30 ppb, would result in a temperature rise of less than 0.55° C. per day, and typically less than 0.2° C. per day (less than the first predetermined rate). However, when a greater concentration of sulfur breakthrough, e.g. greater than 100 ppb, is present in the fuel and/or the amount of sulfur breakthrough continues to increase, the temperature in catalyst bed 208 will increase at the first predetermined rate. In this illustrative example, the first predetermined rate at which the temperature rises is greater than 1.1° C. per day, and the rate of 1.1° C. per day corresponds to a concentration of 200 ppb of sulfur breakthrough in the fuel. In other embodiments, where higher sensitivity is needed, the first predetermined rate may be set at a smaller value, such as greater than 0.55° C. per day, which corresponds to the predetermined concentration of greater than 100 ppb of sulfur breakthrough of fuel. In the fuel cell system of FIG. 2 or in the fuel utilization system of FIG. 1, the large increase in the rate of the temperature rise, i.e. at the first predetermined rate, typically occurs when the desulfurizer is no longer capable of sufficiently desulfurizing the fuel, such as when the operating desulfurizer bed has reached, or is approaching, its sulfur removal capacity. It is understood that the first predetermined rate of the temperature rise in the catalyst bed 208 is not limited to greater than 1.1° C. per day or greater than 0.55° C. per day, and that the first predetermined rate may be varied based on the concentrations of sulfur-containing compounds that can be tolerated by the system being monitored. In addition, a second predetermined rate of temperature increase in the catalyst bed 208 may be used for triggering more severe actions by the controller assembly 501. In the illustrative embodiment described above, the second predetermined rate is greater than 4.4° C. per day, which corresponds to the predetermined sulfur breakthrough concentration of greater than 800 ppb, but it may be varied in other embodiments.

In order to accurately determine the concentration of sulfur breakthrough in the fuel and the rate of increase in the sulfur breakthrough in the fuel, the space velocity and superficial velocity of the fuel flowing through the sulfur breakthrough detector 206b must be controlled. The sensitivity of the sulfur breakthrough detector 206b is significantly improved by providing optimal geometry of the sulfur breakthrough detector and controlling the operating temperature, as described above, as well as by controlling the space velocity and superficial velocity of the fuel through the reforming catalyst bed. In particular, the sulfur breakthrough detector 206b is operated so that the space velocity of the fuel through the reforming catalyst bed is within a defined kinetically-limited range so that any deactivation or poisoning of the reforming catalyst shows up rapidly as loss of reforming capacity and as the temperature drop across the reforming catalyst bed. In this embodiment, the space velocity of the fuel through the reforming catalyst bed is in the range of 30,000/hr and 120,000/hr, with the optimal space velocity being about 90,000/hr. In addition, the operation of the sulfur breakthrough detector 206b is controlled so that the superficial velocity of the fuel through the reforming catalyst bed is sufficiently low to allow for hydrogen back diffusion in order to maintain the reforming catalyst in a reduced state despite the lack of hydrogen in the fuel feedstock. The superficial velocity of the fuel is in the range between 7 and 60 cm/sec, with the optimal superficial velocity being 25 cm/sec. The space velocity and superficial velocity of the fuel are controlled by controlling the flow rate of fuel through the sulfur breakthrough detector and the geometry of the sulfur breakthrough detector. Monitoring by the control assembly as described below is used to signal whether the flow rate is in the correct or expected range.

Referring now to FIG. 3A, a controller assembly 501 which includes one or more control sections and/or one or more controllers, receives temperature readings from the thermal sensors T1 to T5, and determines whether or not the concentration of sulfur breakthrough in the fuel is greater than the predetermined concentration and/or is increasing at a high rate. The controller assembly 501 also controls the heating provided by the heater 206a and determines whether the flow of fuel through the monitoring assembly 206 is stable or constant and sufficiently high so as to provide an accurate sulfur breakthrough determination.

As shown in FIG. 3A, the controller assembly 501 includes a first control section TDY-1, or first controller, which receives temperature readings from temperature sensors T3 and T4 and determines, by comparing these temperature readings over time, the rate at which the temperature is increased in the catalyst bed 208 and whether the rate of the temperature increase is at the first predetermined rate, and also whether the rate is at the second predetermined rate. When the first control section TDY-1 determines that the temperature in the catalyst bed 208 increases at a rate that is less than the first predetermined rate, e.g. 1.1° C. per day (24 hours) or less, the concentration of sulfur breakthrough in the fuel is below the predetermined concentration and is increasing at a slow and constant rate. This indicates that the desulfurizer assembly of the system is operating properly with sufficient desulfurization of the fuel, and that the operating desulfurizer has not reached its absorbent/adsorbent capacity. However, when the first control section TDY-1 determines that the temperature in the catalyst bed 208 is increasing at a rate that is greater than the first predetermined rate, e.g. greater than 1.1° C. per day, then it is determined that the concentration of sulfur breakthrough in the fuel is equal to or greater than the predetermined concentration, indicating a potential problem with the desulfurizer assembly, such as saturation of the operating desulfurizer bed(s). If the first controller TDY-1 determines that the temperature in the catalyst bed 208 is increasing at or above the first predetermined rate, the first controller TDY-1 controls to activate one or more alarms, such as an alarm causing one or more predetermined actions to occur. The one or more alarms include, but are not limited to, activating an alarm or an alarm state, activating an alarm controlling the flow of fuel to the processing assembly of the fuel cell system so as to stop or limit the flow of the presently flowing fuel conveyed to the processing assembly, activating an alarm controlling the supply of fuel to the system so as to stop or limit the flow of fuel to the system, and activating an alarm controlling the desulfurizer assembly so as to redirect the flow of fuel to be desulfurized through another desulfurizer bed and/or to regenerate or replace the desulfurizer bed that has reached its absorbing/adsorbing capacity. In addition, the first controller TDY-1 determines whether the temperature in the catalyst bed 208 is increasing at the second predetermined rate, which is higher than the first predetermined rate, and if so, the first controller TDY-1 activates one or more alarms which have a greater escalation, or greater severity, than the alarm(s) previously activated. For example, if the first controller TDY-1 determines that the temperature in the catalyst bed 208 increases at the second predetermined rate, then TDY-1 may control the system so as to inhibit the flow of fuel to the fuel cell or fuel utilization device, or to inhibit the flow of fuel to the system, or to select an alternate fuel source or redirect the present fuel source to use a back-up desulfurization system.

Operation of the first control section TDY-1 will now be described in more detail. At the start of the monitoring assembly operation, the first control section TDY-1 receives temperature readings from the temperature sensors T3 and T4 and determines the difference between the received temperature readings by subtracting T4 from T3, i.e. T4-T3, to establish an initial temperature difference value TDY_STEADY. In some embodiments, the initial temperature difference value TDY_STEADY is established upon the heat up of the monitoring assembly to set point temperature of T3 and achieving a steady flow rate, by averaging the temperature difference values between T4 and T3 over a predetermined time period of n hours, e.g. 3 hours, and/or upon initial heat up may be further adjusted over another time period, e.g. 24 hours, so as to obtain more accurate readings. After the initial temperature difference value TDY_STEADY is established, the first control section TDY-1 continues to receive and compare temperature readings from the temperature sensors T3 and T4 by subtracting T4 from T3, i.e. T4-T3, so as to continuously obtain temperature difference values TDY_FLOAT. The temperature difference values between T3 and T4 for determining TDY_FLOAT may also be averaged over the predetermined time period of n hours, e.g. 3 hours, so as to eliminate noise and to obtain more accurate values. The first control section TDY-1 then compares the obtained temperature difference values TDY_FLOAT with the previously established initial temperature difference value TDY_STEADY by subtracting TDY_FLOAT from TDY_STEADY, i.e. TDY_STEADY−TDY_FLOAT. The difference values between TDY_FLOAT and TDY_STEADY are continuously determined and monitored by the first control section TDY-1 to determine whether the temperature in the catalyst bed 208 has increased by a threshold amount and/or whether the temperature in the catalyst bed 208 is increasing at the first or the second predetermined rate. Otherwise, the slope of the line T4-T3 versus time may be continuously calculated to provide the same result.

In the present illustrative embodiment, the first control section TDY-1 first determines whether the difference between TDY_STEADY and TDY_FLOAT (TDY_STEADY−TDY_FLOAT) is greater than or equal to a threshold value, and if it is, then TDY-1 activates an alarm state, such as a Hi-alarm state, which indicates that the temperature in the catalyst bed 208 has increased by the threshold amount. The Hi-alarm state continues to be held active by the first control section TDY-1 as long as TDY-1 continues to determine that the difference between TDY_STEADY and TDY_FLOAT is equal to or greater than the threshold value. If, after the Hi-alarm state is activated, the difference between TDY_STEADY and TDY_FLOAT becomes smaller than the threshold value, then the Hi-alarm state is deactivated. In the present illustrative embodiment, the threshold value is 1.1° C., but it may be varied depending on the desired sensitivity of the monitoring assembly and sulfur tolerance of the system with which the monitoring assembly is being used. If the first control section TDY-1 determines that the difference between TDY_STEADY and TDY_FLOAT is less than the threshold value, then the first control section TDY-1 continues to monitor the temperature differences between newly received TE-4 and TE-3 temperature values and comparing them to TDY_STEADY without activating an alarm state, and if an alarm state has been previously activated, TDY-1 deactivates the alarm state.

In the present embodiment, when the first control section TDY-1 determines that the difference between TDY_STEADY and TDY_FLOAT is equal to or greater than the threshold value, the first control section TDY-1 then monitors the change in TDY_FLOAT and determines whether TDY_FLOAT is decreasing at the first predetermined rate, i.e. greater than 2.2° C./day. The rate of TDY_FLOAT drop is proportional to the sulfur breakthrough concentration in the fuel, and thus, a determination that TDY_FLOAT decreases at the first predetermined rate indicates that the sulfur breakthrough concentration in the fuel is greater than the predetermined concentration, i.e. 200 ppb. If the first control section TDY-1 determines that the rate of TDY_FLOAT is at the first predetermined rate, then TDY-1 controls the system being monitored so as to activate an escalated alarm to a Hi-Hi-Alarm, which causes one or more predetermined actions to occur. These predetermined actions include one or more of: activation of the Hi-Hi alarm indicating high sulfur breakthrough concentration in the fuel, controlling the flow of fuel to the system so as to stop or limit the fuel flow to the system, controlling the flow of fuel to the processing assembly so as to stop or limit the fuel flow to the processing assembly, controlling the desulfurizer assembly so as to require changing or regeneration of the operating desulfurizer bed, and controlling the flow of fuel through the desulfurizer assembly so that the fuel is conveyed to another desulfurizer bed. In multiple-fuel systems, which operate on one or more of a plurality of fuels each of which is independently desulfurized, and which can switch from one fuel to another or blend the fuels for continuous use of two or more fuels, the predetermined actions may also include switching operation of the system from one fuel to another by stopping the flow of the one fuel and controlling to supply another fuel to the system, or switching from blended fuel operation to single fuel operation by inhibiting supply of one of the fuels to the system.

In certain embodiments, when the first control section TDY-1 determines that the rate of TDY_FLOAT drop is equal to the first predetermined rate, then the TDY-1, after activating the Hi-Hi-alarm, determines whether the rate of the TDY_FLOAT drop is equal to the second predetermined rate which is greater than the first predetermined rate. A determination that the rate at which TDY_FLOAT is decreasing is equal to the second predetermined rate indicates that the concentration of sulfur breakthrough in the fuel is very high, i.e. 800 ppb, and increasing at a high rate, and that a more severe action is required to prevent sulfur poisoning in the system. If the first control section TDY-1 determines that the rate of TDY_FLOAT drop is equal to the second predetermined rate, then TDY-1 activates a Hi-Hi-Hi alarm, which has an escalation of the Hi-Hi alarm and which causes one or more predetermined actions to be taken by the system. These predetermined actions are more severe than the action(s) taken during activation of the Hi-Hi alarm. For example, the predetermined actions taken in response to the Hi-Hi-Hi alarm include inhibiting the flow of fuel to the fuel cell or fuel utilization device or inhibiting the flow of fuel to the system, and/or tripping of the plant.

If the first control section TDY-1 determines that the rate of TDY_FLOAT drop is less than the first predetermined rate, then the first control section TDY-1 continues to monitor the temperature differences between newly received T4 and T3 temperature values to determine TDY_FLOAT, to compare the new TDY_FLOAT values to TDY_STEADY and to monitor the rate of TDY_FLOAT drop. The steps performed by the controller assembly 501 to control the sulfur breakthrough detector 106a and to monitor the amount of sulfur breakthrough in the fuel are described in more detail below with reference to FIG. 4B.

In accordance with the method described above, the first control section TDY-1 determines whether or not the concentration of sulfur breakthrough in the fuel is greater than the predetermined concentration based on the rate of the temperature increase in the catalyst bed 208, which is related to the rate of sulfur poisoning of the reforming catalyst. Although in the illustrative embodiment described above, the first control section TDY-1 activates an alarm state when the temperature in the catalyst bed 208 increases by 2.2° C. and then escalates the alarm and/or controls to take one or more predetermined actions when the temperature in the catalyst bed 208 increases at the first predetermined rate of more than 2.2° C. per day (24 hours) and when the temperature in the catalyst bed 208 increases at the second predetermined rate of 8.8° C. per day, it is understood that these alarm and action triggering values may be varied depending on accuracy requirements of the system and the sensitivity of the system to sulfur-containing compounds. Thus, for example, when the system has a lower sensitivity to the presence of sulfur-containing compounds, the first predetermined rate of the temperature increase in the catalyst bed 208, and of the corresponding drop in TDY_FLOAT, that triggers one or more predetermined actions to be performed by TDY-1 may be greater than 2.2° C. per day. In addition, the alarms activated and/or actions controlled by the first control section TDY-1 based on the determinations made during monitoring of the temperature differences between T3 and T4 may be varied. However, it is understood that the first control section TDY-1 may be able to activate a series of alarms and/or take a series of actions in an escalating order based on the determined rate of temperature increase in the catalyst bed, or the determined rate of TDY_FLOAT drop, and the corresponding reforming catalyst degradation. Thus, for example, the first control section TDY-1 may only activate a Hi-alarm state when the temperature increases by the threshold amount, alerting an operator of such increase, and may increase the alarm state to Hi-Hi-alarm state when the temperature increases at the first predetermined rate, controlling the system to perform one or more predetermined actions. The controller may further control the system to perform more severe actions, such as tripping of the plant, if the temperature increases at the second predetermined rate, e.g. 8.8° C. per day.

As mentioned above, the controller assembly 501 also controls the heating of the heater 206a so that the fuel gas is heated to the predetermined temperature T3 without overheating the heater 206a as measured at T1 and T2. As shown in FIG. 3A, the controller assembly 501 includes a heater temperature controller TC-1 and a reactor inlet temperature controller TC-2, which control the heater based on the temperatures in the heater 206a and in the reforming catalyst 208, respectively. The temperature controllers TC-1 and TC-2 use temperature readings from temperature sensors T1/T2 and T3, which detect temperatures in the heater 206a and reforming catalyst 208. In particular, the heater temperature controller TC-1 has a set point temperature (SP) which corresponds to the maximum continuous operating temperature of the heater, and receives temperature measurements (process variable, or PV) from one of the temperature sensors T1 or T2. In this illustrative embodiment, the set point temperature of the heater temperature controller TC-1 is 650° C., but it may be varied depending on the type of heater used and desired amount of heating to be provided to the fuel. The reactor inlet temperature controller TC-2 also has a set point temperature (SP) which corresponds to the desired temperature of the reactor inlet, and receives temperature measurements (PV) from the temperature sensor T3. In the present illustrative embodiment, the set point temperature of the reforming catalyst controller TC-2 is 500° C., but it may be varied depending on the desired lower detection limit of the sulfur breakthrough detector as well as the types of sulfur-containing compounds present in the fuel and the types of sulfur-containing compounds being detected. In order to assure that the poisoning reactions occur with all or most of the sulfur-containing compounds in the fuel, the set point temperature in the reforming catalyst should be in the range of 450° C. to 600° C., with the temperature range of 475° C.-550° C. being optimal. Higher temperatures are used to provide lower levels of detection of sulfur breakthrough. For example, operation at 450° C. may detect sulfur breakthrough down to 100 ppb whereas operation at 500° C. may provide detection down to 30 ppb.

As also shown in FIG. 3A, a control variable output (CV) of the heater temperature controller TC-1 and a control variable output (CV) of the reactor inlet temperature controller TC-2 are provided to a low selector 209. The low selector selects the lower output of these two controllers TC-1 or TC-2, so that the heating of the heater 206a is controlled based on the selected lower setting. In this way, overheating of the heater 206a can be avoided, particularly if the fuel flow through the monitoring assembly is low and the temperature in the reactor inlet is not able to achieve the set point of the reactor inlet temperature controller 206a. The heater temperature controller TC-1, the reactor inlet temperature controller TC-2, and the low selector 209 are used for controlling the heater 206a whenever power is provided to the heater 206 as described in more detail below with reference to FIG. 4A.

Finally, the controller assembly 501 also determines whether the fuel flow rate through the sulfur breakthrough monitoring assembly is stable and sufficiently high so as to maintain accurate and precise monitoring of the sulfur breakthrough. As discussed above, the monitoring of the fuel flow rate through the sulfur breakthrough assembly is used to determine if the fuel flow rate is such that the space velocity and superficial velocity of the fuel through the sulfur breakthrough assembly are within the defined ranges. That is, the fuel flow rate is controlled so that the space velocity is in the range of 30,000/hr to 120,000/hr and the superficial velocity is in the range of 7 to 60 cm/sec. As shown in FIG. 3A, the controller assembly 501 includes a second control section TDY-2 which receives temperature measurements from temperature sensors T4 and T5 and determines whether the flow rate is high and stable based on these temperature measurements. In particular, the second control section TDY-2 compares the temperature readings from T4 and T5 by subtracting the T5 temperature measurement from the T4 temperature measurement, i.e. T4–T5, to obtain a temperature difference value dT. The second control section TDY-2 then determines whether the difference dT between these temperature measurements is smaller than a predetermined difference and whether the difference dT varies by more than a predetermined amount. In the present embodiment, the second control section TDY-2 determines whether dT(T4–T5) is smaller than 80° C. and whether or not the variations in dT are greater than 4° C./hr. If TDY-2 determines that the dT is smaller than 80° C. and the variations in dT are smaller than 4° C./hr, then TDY-2 determines that the fuel flow rate through the monitoring assembly is stable and sufficiently high. If it is determined that dT is greater than 80° C., then TDY-2 determines that the flow rate is not high enough for accurate and precise monitoring by the monitoring assembly. In response to this determination, TDY-2 activates one or more alarms, such as an alarm indicating that the flow rate of the fuel should be increased and/or an alarm controlling the system to increase the fuel flow rate through the monitoring assembly. If it is determined that the variations in dT are greater than 4° C., then TDY-2 determines that the flow rate is not sufficiently stable and activates one or more alarms. These alarms may include an alarm indicating that the flow rate is not stable and/or an alarm controlling the monitoring assembly to suspend monitoring of the sulfur breakthrough in the fuel until the flow rate is stabilized. It is noted that the dT alarm values used by TDY-2 are dependent on the design of the device, especially the location of T5 and insulation surrounding T5. The value of 80° C. is therefore exemplary, and other values higher or lower may be more appropriate depending on design of the sulfur breakthrough monitoring assembly.

The temperature differences between T4 and T5 are monitored by TDY-2 concurrently with the monitoring of the temperature differences between T3 and T4 by the first control section TDY-1. In addition to determining whether the flow rate through the sulfur breakthrough detector is stable and sufficiently high, the monitoring by TDY-2 can also be used for confirming determinations of sulfur poisoning by TDY-1. This is done because a sudden increase in the flow rate of fuel through the sulfur breakthrough detector can result in a decreased rate of reforming and therefore in a temperature drop across the reforming catalyst bed, which can be interpreted by TDY-1 as sulfur poisoning. When the temperature drop across the reforming catalyst bed is caused by the increase in the fuel flow rate, the temperature difference between T4 and T5 decreases. However, when the temperature drop across the reforming catalyst bed is caused by sulfur poisoning, the temperature difference between T4 and T5 is nearly constant or may increase slightly. As a result, when TDY-1 determines that TDY_FLOAT (difference between T3 and T4) drops at the first or second predetermined rate, the second control section TDY-2 will also detect a steady or slight increase in the difference between T4 and T5 due to greater heat loss from the fuel in the outlet section of the sulfur breakthrough detector caused by the higher temperature at T4. In certain embodiments, the determination by TDY-2 that the difference between T4 and T5 is increasing at a third predetermined rate can be used to confirm that sulfur poisoning of the reforming catalyst has occurred. In such embodiments, when the first control section TDY-1 determines that TDY_FLOAT is decreasing at the first or second predetermined rate, the control assembly may confirm that the difference between T4 and T5 is steady or slightly increasing prior to performing one or more predetermined actions.

In some embodiments, the stability of the fuel flow rate during operation can be determined based on other variables or measurements, such as based on the temperature at the reactor inlet T3. In particular, the fuel flow rate through the monitoring assembly is determined to be stable and sufficiently high when the temperature of the reactor inlet is stable at or near the temperature set point (SP), e.g. temperature measured by T3 is at SP=500° C.±3° C. In the embodiment of FIG. 1, the fuel flow rate is controlled by the fuel flow controller 15. Conversely, in the embodiment of FIG. 2, the fuel flow is driven by the pressure drop in the parallel fuel processing system 110, and therefore will vary depending on the flow rate of humidified fuel through the parallel fuel processing system, which is mainly dependent on fuel cell power plant output. Particularly in the embodiment of FIG. 2, it is useful to use T3 and TDY-2 to confirm the desired and stable flow rate is present.

A second embodiment of the sulfur breakthrough monitoring assembly 306, which can be used in the fuel utilization system of FIG. 1 or in the fuel cell system of FIG. 2, is shown in FIG. 3B. The sulfur breakthrough monitoring assembly 306 of FIG. 3B is suitable for monitoring sulfur breakthrough in fuel that includes oxygen, such as anaerobic digester gas (ADG) or landfill gas which often contains up to 1% oxygen. The sulfur breakthrough detector of FIG. 3B can accept fuel with up to 5% oxygen. As in the first embodiment of the monitoring assembly 206 shown in FIG. 3A, the monitoring assembly 306 of FIG. 3B comprises a heater 306a which receives fuel and water (FIG. 1) or humidified fuel (FIG. 2) and heats the fuel to the predetermined temperature. As discussed above, if the monitoring assembly 306 is used in the system of FIG. 1, the fuel flow is independently controlled in the fuel flow controller 15 while the water is independently controlled in the water flow controller 8, and the fuel and water are then sent to the heater 6a, while the monitoring assembly 306 used with the system of FIG. 2 receives humidified fuel from the humidifier 108, and the humidified fuel is heated in heater 106a. In the present embodiment, the heater heats the fuel such that upon deoxidation of any oxygen that may be present in the fuel, the predetermined temperature at the reactor inlet is between 450° C. and 600° C., and is preferably between 475° C. and 550° C. Thus, in the present embodiment, the control point for the predetermined temperature is measured toward the exit of the deoxidizer catalyst by temperature element T4 at which point any oxygen in the fuel will have reacted with the fuel thereby heating the fuel. For example, the temperature rise from each 0.1% oxygen in the fuel may be 3° C. or 4° C., depending on the steam to carbon ratio and carbon dioxide level in the fuel. As in the first embodiment, the predetermined temperature in this embodiment may be varied based on the desired detection level as well as the types of sulfur-containing compounds being monitored and the system requirements. The construction of the heater 306a in this embodiment is similar to the heater 206a of FIG. 3A and detailed description thereof is omitted.

As shown in FIG. 3B, the monitoring assembly further comprises a sulfur breakthrough detector (SBD) 306b, which receives heated fuel from the heater 306a and further heats the fuel through deoxidation in the deoxidizer catalyst 309. The SBD 306b comprises a housing 307, a deoxidizing catalyst bed 309 and a reforming catalyst bed 308, with both beds being disposed in the housing 307. The deoxidizing bed 309 and the reforming bed 308 are disposed in series so that the heated fuel first passes through the deoxidizing bed 309, where oxygen content in the fuel is removed, and then through the reforming bed 308, in which the fuel is reformed so as to increase hydrogen content in the fuel. The dimensions of the housing 307 and the catalyst beds 309, 308 may vary dependent on the amount of fuel flow to be conveyed through the monitoring assembly and the desired sensitivity of the monitoring assembly 306.

As discussed above, when the monitoring assembly is used with a fuel cell system of FIG. 2, about 0.2% of the total humidified fuel is conveyed from the connecting line 107 to the sulfur breakthrough monitoring assembly at a flow rate of about 6 slpm, and in certain embodiments, the humidified fuel is conveyed to the monitoring assembly at a flow rate of 0.5 to 3 slpm. Also, when the monitoring assembly is used with the fuel utilization system of FIG. 1, the fuel is conveyed to the monitoring assembly at a flow rate of 0.5 to 2 slpm and is blended with water for humidification by the addition of water from the water flow controller 8 prior to being heated in the heater 306a. In this illustrative embodiment, the housing of the sulfur breakthrough monitoring assembly 306 is a substantially cylindrical housing formed from metallic materials with a diameter of 1 inch (2.54 cm) and a height of 3 inches (7.62 cm). Also in this embodiment, the housing houses therein the deoxidizing catalyst bed 309 which includes 7.5 grams of deoxidizing catalyst with a depth of about 25 mm, and the reforming catalyst bed 308 which includes 5 grams of nickel-based reforming catalyst with a depth of about 9 mm. The deoxidizing catalyst may be in the form of pellets or the like supported by a screen disposed in the housing and separating the deoxidizing bed from the reforming catalyst bed. The reforming catalyst having the properties described above with respect to the first embodiment of FIG. 3A is also used in the reforming catalyst bed 308 of the second embodiment of FIG. 3B and thus, detailed description thereof is omitted.

As shown in FIG. 3B, temperatures in the sulfur breakthrough detector 306b are sensed and monitored by a plurality of temperature sensors T3, T4, T5 and T6, which can be in the form of thermocouples. A third temperature sensor, or thermocouple, T3 senses the temperature of the heated fuel flowing through an inlet portion 307a of the housing 307 and prior to entering the deoxidizing catalyst bed 309. A fourth temperature sensor, or thermocouple, T4 senses the temperature in the deoxidizing catalyst bed 309, a fifth temperature sensor, or thermocouple, T5 senses the temperature in the reforming catalyst bed 308 and a sixth temperature sensor, or thermocouple, T6 senses the temperature of the fuel flowing through an outlet portion 307b of the housing 307 after the fuel has passed through the reforming catalyst bed 308. The temperatures sensed by the temperature sensors T3, T4, T5 and T6 are used for monitoring sulfur breakthrough concentration in the fuel and for determining whether the amount of sulfur breakthrough in the fuel is increasing at a high rate. As also described, the temperatures sensed by the temperature sensors T1 to T6 may also be used for controlling the heating of the heater and for determining whether the fuel flow rate through the sulfur breakthrough monitoring assembly is sufficient to maintain accurate and precise monitoring of the sulfur breakthrough. The fuel flow rate monitoring is used for controlling the flow of fuel through the sulfur breakthrough assembly 306b so that the space velocity of the fuel through the reforming catalyst bed 308 is between 30,000/hr and 120,000/hr and the superficial velocity of the fuel through the reforming catalyst is between 7 cm/sec and 60 cm/sec.

During operation of the sulfur breakthrough monitoring assembly 306, desulfurized and humidified fuel portion is heated to a constant predetermined temperature by the heater 306a and thereafter guided through the sulfur breakthrough detector 306b. In the sulfur breakthrough detector 306b, the heated fuel is conveyed through the deoxidizing catalyst bed 309, where the oxygen content in the fuel is removed using the deoxidizing catalyst, and then the deoxidized fuel is partially reformed by the reforming catalyst in the reforming catalyst bed 308 before being output from the housing 307 of the sulfur breakthrough detector 306b. As discussed above, the temperature in the reforming catalyst bed 308 is dependent on the rate of the reforming process by which the fuel is reformed, which is directly related to the condition of the reforming catalyst in the reforming catalyst bed 308. Therefore, the concentration of sulfur breakthrough in the fuel and the rate of increase of the sulfur breakthrough in the fuel are monitored by detecting and monitoring the increase in the temperature in the reforming catalyst bed 308.

Similar to the first embodiment of FIG. 3A, the monitoring assembly 306 of FIG. 3B has the controller assembly 501, which includes one or more control sections and/or one or more controllers that receive temperature readings from the thermal sensors T1 to T6 and determine whether or not the concentration of sulfur breakthrough in the fuel is greater than the predetermined concentration. As shown in FIG. 3B, the controller assembly 501 includes a first control section TDY-1, or first controller, which receives temperature readings from temperature sensors T4 and T5 and determines, by comparing these temperature readings over time, the rate at which the temperature is increased in the reforming catalyst bed 308, whether the rate of the temperature increase in the reforming catalyst bed 308 is equal to the first predetermined rate and whether the rate is equal to the second predetermined rate. As discussed herein above, in the present illustrative embodiment, the first predetermined rate is greater than 1.1° C. per day (24 hours) and the second predetermined rate is greater than 4.4° C. per day, which correspond to sulfur breakthrough concentrations of greater than 200 ppb and greater than 800 ppb, respectively. When greater sensitivity to sulfur breakthrough is required, the first predetermined rate is greater than 0.55° C. per day, corresponding to sulfur breakthrough concentration of greater than 100 ppb. When the first control section TDY-1 determines that the temperature in the reforming catalyst bed 308 increases at a rate smaller than the first predetermined rate, e.g. 1.1° C. per day (24 hours) or less, the amount of sulfur breakthrough in the fuel is smaller than the predetermined concentration. This determination indicates that the desulfurizer assembly or desulfurizing system of the system is operating properly with sufficient desulfurization of the fuel, and that the operating desulfurizer has not reached its absorbent/adsorbent capacity. In contrast, when the first control section TDY-1 determines that the temperature in the reforming catalyst bed 308 is increasing at the first predetermined rate, e.g. greater than 1.1° C. per day, then it is determined that the concentration of sulfur breakthrough in the fuel is equal to or greater than the predetermined concentration. This determination indicates a potential problem with the desulfurizer assembly or desulfurizing system, such as saturation of the operating desulfurizer bed(s).

As discussed above with respect to the first embodiment, if the first controller TDY-1 determines that the temperature in the reforming catalyst bed 308 is increasing at the first predetermined rate, the first controller TDY-1 controls to activate one or more alarms, such as an alarm causing one or more predetermined actions to occur. These one or more alarms include, but are not limited to, activating a HI alarm or an alarm state, activating an alarm controlling the flow of fuel to the processing assembly of the fuel cell system so as to stop or limit the flow of fuel conveyed to the processing assembly, activating an alarm controlling the supply of fuel to the system so as to stop or limit the flow of fuel to the system, and activating an alarm controlling the desulfurizer assembly so as to redirect the flow of fuel to be desulfurized through another desulfurizer bed and/or to regenerate or replace the desulfurizer bed that has reached its absorbing/adsorbing capacity. In addition, if the first control section TDY-1 determines whether the temperature in the reforming catalyst bed 308 is increasing at the second predetermined rate, which is higher than the first predetermined rate, then TDY-1 activates one or more escalated alarms, such as a Hi-Hi alarm, which causes one or more predetermined actions of increased severity to occur. As discussed above, these predetermined actions may include inhibiting the flow of fuel to the fuel cell or fuel utilization device, inhibiting the flow of fuel to the system, and/or tripping the system.

The operation of the first control section TDY-1 in this embodiment is similar to the operation of the first control section TDY-1 of the first embodiment described above, except that the TDY-1 makes its determinations based on the temperature readings from the temperature sensors T4 and T5. Specifically, the initial temperature difference value TDY_STEADY is established by the first control section TDY_1 in this embodiment by determining the difference between received temperature readings from T4 and T5 by subtracting T5 from T4, i.e. T4–T5. As in the first embodiment, the TDY_STEADY value can be established by averaging the temperature difference values between T4 and T5 over a predetermined time period of n hours, such as 3 hours, and may be further adjusted over another time period, such as 24 hours. After TDY_STEADY is established, the first control section TDY-1 continuously obtains temperature difference values TDY_FLOAT by comparing received temperature readings from the temperature sensors T4 and T5 by subtracting T5 from T4, i.e. T4–T5. As in the first embodiment, the temperature difference values between T4 and T5 for determining TDY_FLOAT may be averaged over n hours, such as 3 hours. The TDY_STEADY and continuously determined TDY_FLOAT values are then compared and TDY_FLOAT values are monitored as described above to determine whether the temperature in the reforming catalyst bed 308 has increased by the threshold amount, e.g. 2.2° C., and/or whether the temperature in the reforming catalyst bed 308 is increasing at the first predetermined rate and at the second predetermined rate. Since the operation of the first control section TDY-1 in this embodiment is only different in the temperature sensor readings used by the first control section TDY-1, i.e. T4 and T5, for determining TDY_FLOAT and TDY_STEADY, and is the same in other respects to the operation of the first control section TDY-1 of the first embodiment described above, a further detailed description thereof will be omitted. In addition, the operation of controller assembly 501 to control the sulfur breakthrough detector 306a and to monitor the concentration of sulfur breakthrough in the fuel are described in more detail below with reference to FIG. 4B.

As in the first embodiment of FIG. 3A, it is understood that the alarm and action triggering values are not limited to 2.2° C. as the threshold temperature increase, greater than 2.2° C. per day as the first predetermined rate and greater than 8.8° C. per day or greater as the second predetermined rate. These values may be varied depending on the system requirements, such as the system's accuracy requirements, and the sensitivity of the system to sulfur-containing compounds. In addition, the alarms activated and/or actions controlled by the first control section TDY-1 based on the determinations made during monitoring of the temperature differences between T4 and T5 may be varied.

In addition to monitoring the rate at which the sulfur breakthrough in the fuel increases, the controller assembly 501 also controls the heating provided by the heater 306a and determines whether the flow rate of fuel through the monitoring assembly 306 is stable or constant and sufficiently high so as to provide an accurate sulfur breakthrough determination. The controller assembly 501 in FIG. 3B includes a heater temperature controller TC-1 and a deoxidizing catalyst temperature controller TC-2, which control the heater based on the temperatures in the heater 306a and in the deoxidizing catalyst bed 309, respectively. The temperature controllers TC-1 and TC-2 use temperature readings from temperature sensors T1/T2 and T4, which detect temperatures in the heater 306a and deoxidizing catalyst 309.

The operation of the heater temperature controller TC-1 and the deoxidizing catalyst temperature controller TC-2 of this embodiment are similar to the operation of the heater temperature controller TC-1 and the reforming catalyst temperature controller TC-2 of the first embodiment. As in the first embodiment, each temperature controller TC-1 and TC-2 has a set point temperature (SP) which correspond to the desired temperatures in the heater and in the deoxidizing catalyst bed 309, respectively. An exemplary set point temperature for TC-1 is 650° C., while an exemplary set point temperature for TC-2 is 500° C. However, these set point temperatures may be varied based on the desired amount of heating to be provided by the heater to the fuel, and based on the desired detection level for sulfur breakthrough as well as the types of sulfur-containing compounds being monitored. To assure that the poisoning reactions occur with all or most of the sulfur-containing compounds in the fuel, the set point temperature for TC-2 should be in the range of 450° C. to 600° C., and preferably 475° C.-550° C. As discussed above, control variable outputs (CV) of the temperature controllers TC-1 and TC-2 are provided to a low selector 310 which selects the lower output of these temperature controllers so as to prevent overheating of the heater. The heating of the heater 306a is controlled based on the selected lower setting. As mentioned above, the control of the heater 306a during the system's start-up operation are described below with reference to FIG. 4A.

Finally, the controller assembly 501 also determines whether the fuel flow rate through the sulfur breakthrough monitoring assembly is stable and sufficiently high so as to maintain accurate and precise monitoring of the sulfur breakthrough. This determination is performed by a second control section TDY-2 which receives temperature measurements from temperature sensors T5 and T6 and determines whether the flow rate is high and stable based on these temperature measurements. The determinations by TDY-2 may also be used to confirm the determinations of sulfur poisoning by TDY-1 as described above. The operation of the second control section TDY-2 in this embodiment is similar to the operation of TDY-2 of the first embodiment, and therefore, detailed description thereof is omitted.

As shown in FIG. 3B, the control assembly 501 also includes a third control section TDY-3 which receives temperature readings from temperature sensors T3 and T4 and determines the difference between the T3 and T4 readings. Based on the differences between T3 and T4 readings, the third control section TDY-3 can determine the level of oxygen in the fuel. In FIG. 3A T3 and T4 are used for determining sulfur breakthrough. In FIG. 3B, T3 and T4 are used to determine oxygen content of the fuel and T4 and T5 are used to determine sulfur breakthrough.

In some embodiments, the stability of the fuel flow rate during operation can be determined based on other variables or measurements, including based on the temperature in the reforming catalyst bed, based on the fuel cell power plant load, and by independent fuel flow measurement such as by using a flow meter, all of which are described above.

Figure 4A:
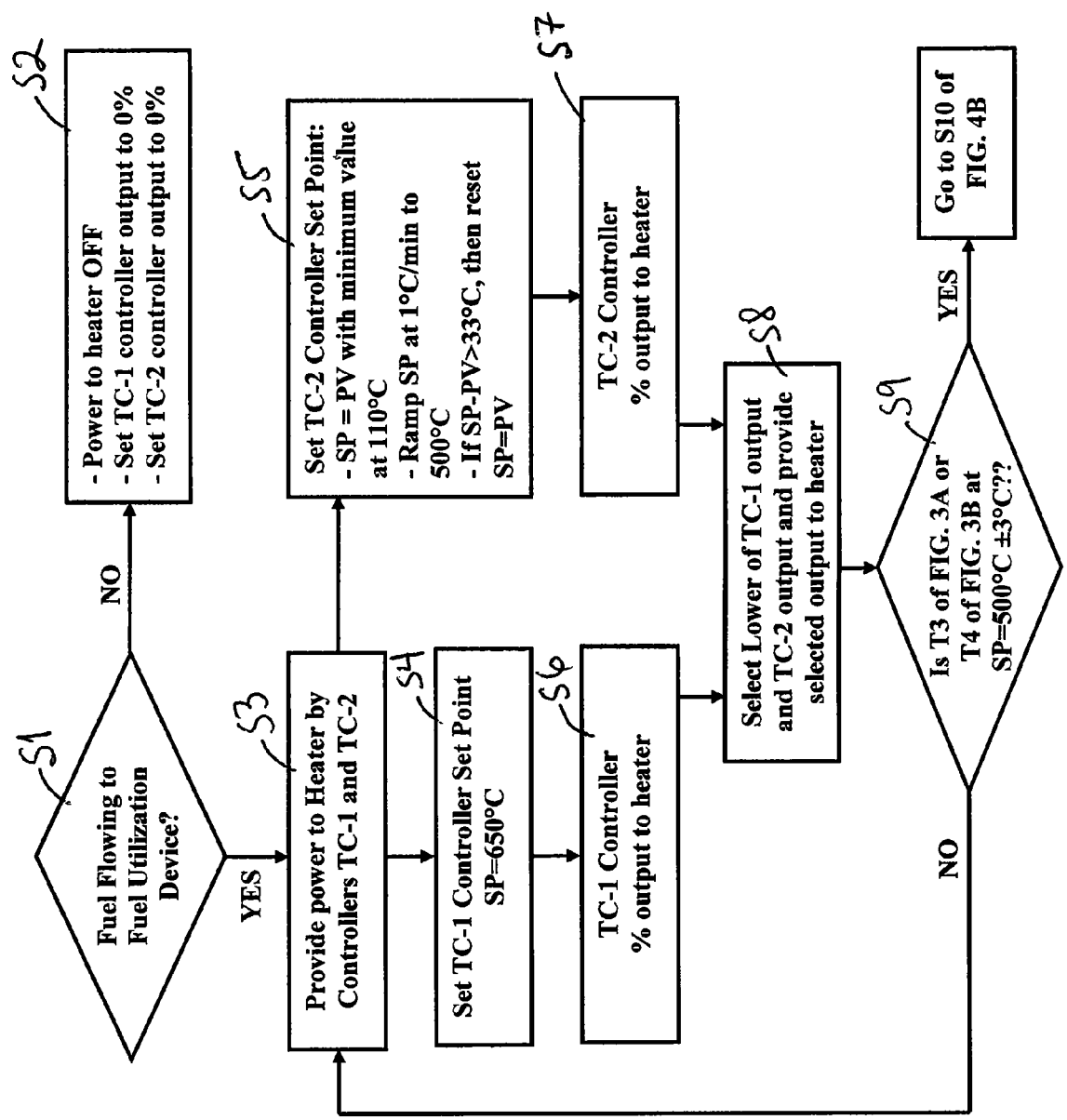
FIG. 4A shows a flow diagram for controlling the heater of sulfur breakthrough monitoring assembly of FIGS. 3A and 3B as applied in FIG. 1 or FIG. 2.
Figure 4B:
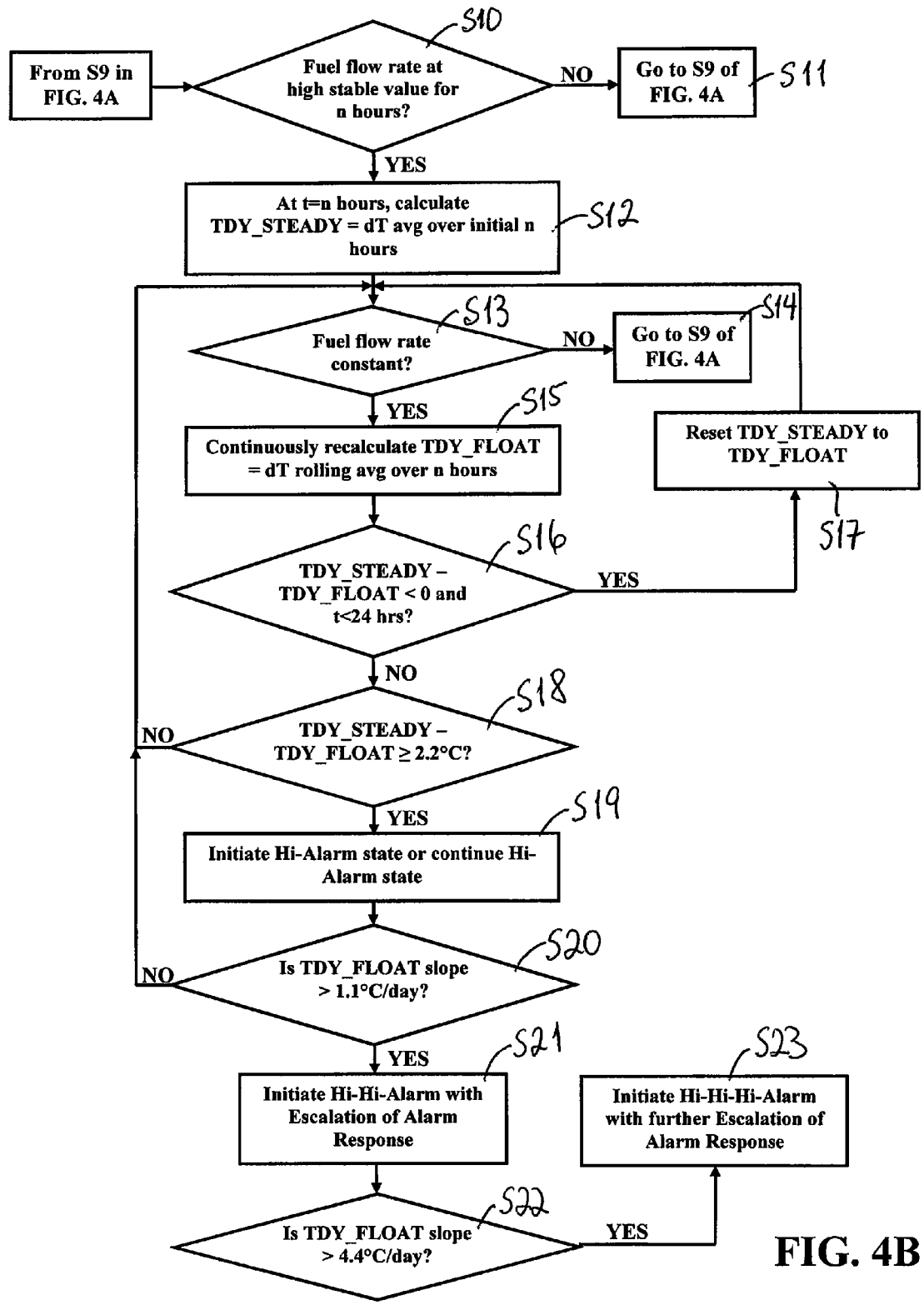
FIG. 4B shows a flow diagram for operating and controlling the sulfur breakthrough monitoring assembly of FIGS. 3A and 3B as applied in FIG. 1 or FIG. 2.

The operation of the controller assembly 501 is shown in FIG. 4A, which shows a flow diagram of controlling the heater 206a, 306a of the monitoring assembly during start-up and operation of the system, and in FIG. 4B, which shows a flow diagram of monitoring the sulfur breakthrough in the fuel based on the temperatures sensed in the sulfur breakthrough detector 206b, 306b. As shown in FIG. 4A, when the operation of the system which uses the monitoring assembly 6, 106, 206a, 306a is started, the controller assembly 501 of the monitoring assembly determines whether or not fuel is flowing to the system in a first step S1. This determination may be made based on one or more signals from the system or by using a flow meter. If the controller assembly 501 determines in step S1 that the fuel is not flowing, then the operation proceeds to step S2 in which power to the heater is turned OFF and outputs of both temperature controllers TC-1 and TC-2 are set to 0%. After step S2, the controller assembly 501 operation returns to the first step S1 to monitor for fuel flow. If in step S1 it is determined that the fuel is flowing, then the operation of the controller assembly proceeds to step S3 in which power is enabled to the heater as controlled by temperature controllers TC-1 and TC-2. In this illustrative embodiment, the controllers TC-1 and TC-2 provide 120V of power to the heater 6a, 106a, 206a, 306a. Operation of the controller assembly then proceeds to steps S4 and S5 to determine the percent power to provide to the heater. In step S4, the heater temperature controller TC-1 set point is set to a first predetermined temperature, which corresponds to a desired maximum allowable temperature of the heater. In this embodiment, the set point for the heater is set by TC-1 to 650° C., but may be varied in other embodiments depending on the heating requirements. Once the TC-1 set point is set in step S4, in step S6, the controller TC-1 produces a percent output to the heater. For example, if the heater temperature is below set point, TC-1 output will increase, and if the heater temperature is above set point, the TC-1 output will decrease.

In parallel with the actions in steps S4 and S6, steps S5 and S7 take place. In step S5, the set point of the temperature controller TC-2 is ramped up until the set point reaches a second predetermined temperature, which corresponds to a desired temperature of the inlet region above the reforming catalyst bed as measured at T3 in the embodiment of FIG. 3A or to a desired temperature of the deoxidizing catalyst bed as measured by T4 in the embodiment of FIG. 3B. In particular, the set point (SP) of the TC-2 controller is first set to be equal to the process variable (PV), starting with a minimum value of 110° C. The process variable (PV) is the actual measured temperature in the inlet region above the reforming catalyst bed in the embodiment of FIG. 3A and the deoxidizing catalyst bed in the embodiment of FIG. 3B. The SP of the TC-2 controller is then ramped up at a rate of 1° C. per minute until SP reaches 500° C. If at any point during the ramping of the SP, the difference between the SP and the PV is greater than 33° C., i.e. SP-PV>33° C., then the SP is reset so that the SP is equal to the PV, i.e. SP=PV. This ramping of the SP and resetting of SP if PV lags behind the SP by more than 33° C. provides for gradual heating up of the catalyst in the sulfur breakthrough detector. It is understood that the temperature difference triggering the reset of the SP, i.e. 33° C., is illustrative and may be varied depending on the system requirements.

After the set point of the TC-2 controller is set in step S5, in step S7 the controller TC-2 produces a percent output to the heater. For example, if the measured temperature PV is below set point, TC-2 output will increase, and if the measured temperature PV is above set point, the TC-2 output will decrease.

In step S8, the TC-1 output from step S6 is compared to the TC-2 output from step S7, and the lesser of the two outputs is selected as the final output to be sent to the heater, e.g., in a low selector 209 of FIGS. 3A and 310 of FIG. 3B. As mentioned above, by selecting the lower of the TC-1 and TC-2 controller outputs, the low selector prevents overheating of the heater, particularly when the fuel flow rate through the monitoring assembly is low.

The operation of the controller assembly 501 then proceeds to step S9 in which the controller assembly determines whether the temperature sensed by the third temperature sensor T3 of FIG. 3A or the fourth temperature sensor T4 of FIG. 3B is equal to 500° C. or is around 500° C., i.e. 500±3° C. As discussed above, the third temperature sensor T3 senses the temperature in the inlet region above the reforming catalyst bed in the monitoring assembly of FIG. 3A, and in the monitoring assembly of FIG. 3B, the fourth temperature sensor T4 senses the temperature in the deoxidizing catalyst bed. If it is determined that the temperature sensed by the third temperature sensor T3 of FIG. 3A or the fourth temperature sensor T4 of FIG. 3B is not equal to, or around, 500° C., then the operation of the controller assembly 501 returns to step S3. If it is determined that the temperature sensed by the third temperature sensor T3 of FIG. 3A or the fourth temperature sensor T4 of FIG. 3B is equal to 500° C.±3° C., then the operation of the controller assembly proceeds to step S10 of FIG. 4B. Although in step S9, the set point temperature of the third temperature sensor T3 of FIG. 3A or the fourth temperature sensor T4 of FIG. 3B is 500° C., it is understood that this set point temperature is illustrative and may be varied depending on the requirements of the system and the monitoring assembly. The set point temperature in step S9 can be selected from a range of temperatures between 450 and 600° C., and preferably between 475 and 550° C. In addition, the variability of the temperature may be smaller or larger than 3° C., depending on the system requirements and how the fuel flow rate through the monitoring assembly is determined.

After the temperature above the reforming catalyst bed (either above the reforming bed in FIG. 3A or the deoxidizing bed in FIG. 3B) sensed by the temperature sensor T3 of FIG. 3A or T4 of FIG. 3B reaches 500° C.±3° C., the operation of the controller assembly 501 proceeds to step S10 of FIG. 4B which shows a flow diagram for operating and controlling the sulfur breakthrough monitoring assembly of FIGS. 3A and 3B. In step S10, the controller assembly 501 determines whether the fuel flow rate to the sulfur detection monitoring assembly is at a high stable value for a predetermined time period of n hours. The predetermined time period in this illustrative embodiment is 3 hours, but may be varied depending on the system requirements. As described above with respect to FIGS. 3A and 3B, there are several ways of determining whether the fuel flow rate is at a high stable. In some embodiments, this determination is accomplished by monitoring the measurements of the third temperature sensor T3 of FIG. 3A or the fourth temperature sensor T4 of FIG. 3B to determine whether the temperature sensor readings are at or near the set point value, e.g. 500° C.±3° C., for n hours, e.g. for 3 hours. In other embodiments, the stability and sufficiency of the fuel flow rate is determined by comparing the temperatures sensed by the T4 and T5 temperature sensors in the embodiment of FIG. 3A or by comparing the temperatures sensed by the T5 and T6 temperature sensors in the embodiment of FIG. 3B to obtain a temperature difference value dT and by determining whether dT is smaller than 30° C. and whether dT variation over the n hours is less than ±4° C. Also, in some embodiments, the stability and sufficiency of the fuel flow rate are determined by monitoring the fuel cell power plant load output and determining whether the load output is stable over the n hours. For example, the fuel flow stability and sufficiency can be determined by monitoring whether the load output of the fuel cell power plant is stable at 130 kW over the period of 3 hours. Finally, in other embodiments, the stability and sufficiency of the fuel flow rate can be determined by independent fuel flow measurement and control, such as by using a flow meter and a flow control member.

If it is determined in step S10 that the fuel flow rate is not at a high stable value, then the operation of the controller assembly proceeds to step S11 in which the operation returns to step S9 of FIG. 4A. If the fuel flow rate is determined in step S10 to be at a high and stable value for n hours, then the operation proceeds to step S12 in which TDY_STEADY is calculated over the initial time period of t=n hours. In the first embodiment of the monitoring assembly shown in FIG. 3A, TDY_STEADY is determined by subtracting the temperature reading of T4 temperature sensor from the temperature reading of T3, i.e. T3−T4, and averaging the temperature difference of T3-T4 over the initial n hours, e.g. 3 hours. In the second embodiment of the monitoring assembly of FIG. 3B, TDY_STEADY is determined by subtracting the temperature reading of T5 from the temperature reading of T4, i.e. T4−T5, and averaging the temperature difference of T4−T5 over the initial n hours, e.g. 3 hours.

After calculating TDY_STEADY, the operation of the controller assembly 501 proceeds to step S13 to determine whether the fuel flow rate is constant. This determination is the same or similar to the determination in step S10. If the fuel flow rate is not constant in step S13, then the operation proceeds to step S14 so as to return to step S9 of FIG. 4A. If the fuel flow rate is determined to be constant, then the operation of the control assembly proceeds to step S15 to calculate, and to continuously re-calculate, TDY_FLOAT on a rolling average over the time periods of n hours. As discussed above with respect to the calculation of TDY_STEADY, the calculation of TDY_FLOAT in the first embodiment of FIG. 3A is performed by comparing temperature measurements from T4 and T3, i.e. T3−T4, and averaging these temperature differences over n hours after the initial n hours, e.g. over 3 hour periods. The calculation of TDY_FLOAT in the second embodiment of FIG. 3B is performed by comparing the temperature measurements from T5 and T4, i.e. T4-T5, and averaging these temperature differences over n hours after the initial n hours, e.g. over 3 hours.

After TDY_FLOAT is calculated, or re-calculated, the operation proceeds to step S16 to compare TDY_FLOAT with TDY_STEADY and to determine whether TDY_STEADY−TDY_FLOAT<0 during the initial 24 hours, i.e. if TDY_FLOAT is greater than TDY_STEADY. If it is determined in S16 that TDY_FLOAT is greater than TDY_STEADY within the initial 24 hour period, then the operation proceeds to step S17 in which TDY_STEADY is reset to be equal to the greater value of the calculated TDY_FLOAT, and then returns to step S13. If TDY_FLOAT is less than or equal to TDY_STEADY, i.e. TDY_STEADY−TDY_FLOAT≥0, then the operation proceeds to step S18.

In step S18, the calculated TDY_FLOAT is compared to the previously established TDY_STEADY from step S12 or S17 to determine whether TDY_FLOAT is at least 2.2° C. smaller than TDY_STEADY, that is, whether TDY_STEADY−TDY_FLOAT≥2.2° C. If TDY_STEADY−TDY_FLOAT is smaller than 2.2° C., then the operation returns to step S13 described above, and any Hi-alarm state previously activated is removed or inactivated. However, if it is determined that TDY_STEADY−TDY_FLOAT is equal to or greater than 2.2° C., then a Hi-alarm state is activated in step S19 or the Hi-alarm state is continued in step S19 if it has been previously activated. This initial Hi-alarm state indicates that sulfur is present, but since there is no time associated with achieving the 2.2° C. drop, this level is not quantitative. This Hi-alarm state functions as a trigger mechanism, or enabler, for the Hi-Hi and Hi-Hi-Hi alarm states to be discussed below. If only the Hi-alarm state comes in but the HiHi and HiHiHi do not, then the sulfur breakthrough concentration is determined to be below the first predetermined value, in this case corresponding to 200 ppb.

In step S20, the calculated TDY_FLOAT is monitored to determine whether the rate at which TDY_FLOAT decreases, or the slope of TDY_FLOAT, is equal to the first predetermined rate. As shown in FIG. 4B, in the present embodiment the first predetermined rate is greater than 1.1° C. per day (24 hours), and in step S20, the controller assembly determines whether the slope of TDY_FLOAT is decreasing at the rate that is greater than 1.1° C. per day. In some embodiments, TDY_FLOAT being monitored is first averaged over a predetermined time period, such as 3 hours, in order to reduce temperature signal variation and to provide more representative average readings. If the controller assembly determines in step S20 that the rate of the TDY_FLOAT decreases at a rate lower than the first predetermined rate, then the operation proceeds to step S13. However, if it is determined in step S20 that the rate of TDY_FLOAT drop is equal to or greater than the first predetermined rate, then the operation proceeds to step S21 in which a Hi-Hi alarm is activated and an escalated alarm response is performed by the controller assembly 501. As discussed above, the Hi-Hi alarm with the escalated alarm response comprises one or more predetermined actions, such as controlling to limit or inhibit fuel flow to the system, activation of an alarm indicating that the desulfurizer needs to be replaced and/or regenerated, controlling to limit or inhibit fuel flow through the operating desulfurizer and/or redirecting the fuel flow to another desulfurizer in standby mode, and/or switching the fuel provided to the system in dual fuel systems.

After initiation of the Hi-Hi alarm in S21, the operation proceeds to step S22 in which the controller assembly determines whether the rate at which TDY_FLOAT decreases, or the slope of TDY_FLOAT, is equal to the second predetermined rate. As shown in FIG. 4B, in the present embodiment the second predetermined rate is greater than 4.4° C. per day (24 hours), and in step S22, the controller assembly determines whether the slope of TDY_FLOAT is decreasing at the rate that is greater than 4.4° C. per day. If it is determined in step S22 that the rate of TDY_FLOAT drop is equal to the second predetermined rate, then the operation proceeds to step S23 in which a Hi-Hi-Hi alarm is activated and a further escalated alarm response is performed by the controller assembly 501. As discussed above, the Hi-Hi-Hi alarm with the further escalated alarm response comprises one or more predetermined actions, which are more severe than the actions taken in step S21, and which may include controlling to limit or inhibit fuel flow to the system, controlling to limit or inhibit fuel flow to the fuel cell or the fuel utilization device, or tripping the system.

After the Hi-Hi alarm is activated and/or predetermined actions are performed by the controller assembly 511 in step S21, and if it is determined in step S22 that the rate of TDY_FLOAT drop is less than the second predetermined rate, then the controller assembly 511 will wait until the Hi-Hi alarm is deactivated and normal operation of the system resumes. Also, after the Hi-Hi-Hi alarm is activated and/or the predetermined actions are performed by the controller assembly in step S23, then the controller assembly 511 will also wait until the Hi-Hi-Hi alarm is deactivated and normal operation resumes. During these waiting time periods following step S22 or step S23, the monitoring assembly may continue to operate and to determine the rate at which the TDY_FLOAT is increasing. In other embodiments, the monitoring assembly may be placed into standby or may be turned off by stopping the supply of fuel to the monitoring assembly and turning OFF the power to the heater, particularly if, after step S23, the fuel supply to the system is turned off. After the Hi-Hi alarm and/or Hi-Hi-Hi alarm are deactivated and the system resumes normal operation, the operation of the monitoring assembly returns to step S9 of FIG. 4A if the monitoring assembly continued operating during the Hi-Hi alarm state or Hi-Hi-Hi alarm state, or to step S1 of FIG. 4A if the monitoring assembly was in standby or turned off before deactivation of the Hi-Hi alarm state or of the Hi-Hi-Hi alarm state.

In the illustrative embodiment described above, the first and second predetermined rates that trigger activation of the Hi-Hi-alarm state and Hi-Hi-Hi alarm state, respectively, are 1.1° C. per day and 4.4° C. per day. However, as mentioned above, these predetermined rates may be varied depending on the system requirements and the desired sensitivity of the monitoring assembly.

Although not shown in FIGS. 4B and 4A, the controller assembly 501 in some embodiments also determines and outputs a quantitative value of the concentration of sulfur-containing compounds present in the fuel based on the rate of drop in TDY_FLOAT. In such embodiments, the amount or concentration of sulfur-containing compounds is determined based on the rate of TDY_FLOAT drop, so that the controller assembly 501 determines the concentration of sulfur-containing compounds in the fuel by correlating the slope of the TDY_FLOAT over time to the amount or concentration of sulfur-containing compounds. In the present illustrative embodiment, the first predetermined rate of TDY_FLOAT drop is 1.1° C./day, which corresponds to 200 ppb concentration of sulfur-containing compounds in the fuel. Based on this correspondence, the controller assembly 501 can determine the concentration of sulfur-containing compounds in the fuel when the rate of TDY_FLOAT is determined. Outputting of the concentration of sulfur-containing compounds in the fuel by the monitoring assembly enables an operator of the system to determine whether or not the desulfurizer assembly is operating properly and whether or not any of the desulfurizer beds needs, or will need, to be changed or regenerated. In addition, during automatic operation, the controller assembly would be able to determine, based on the determined sulfur-containing compound concentration in the fuel, whether or not to activate one or more alarms.

As mentioned above, in certain embodiments, the controller assembly also determines the rate at which the sulfur breakthrough in the fuel is increasing. In such cases, the controller assembly monitors the changes in the slope of TDY_FLOAT over time and based on these changes, determines the rate of sulfur breakthrough increase in the fuel.

Figure 5:
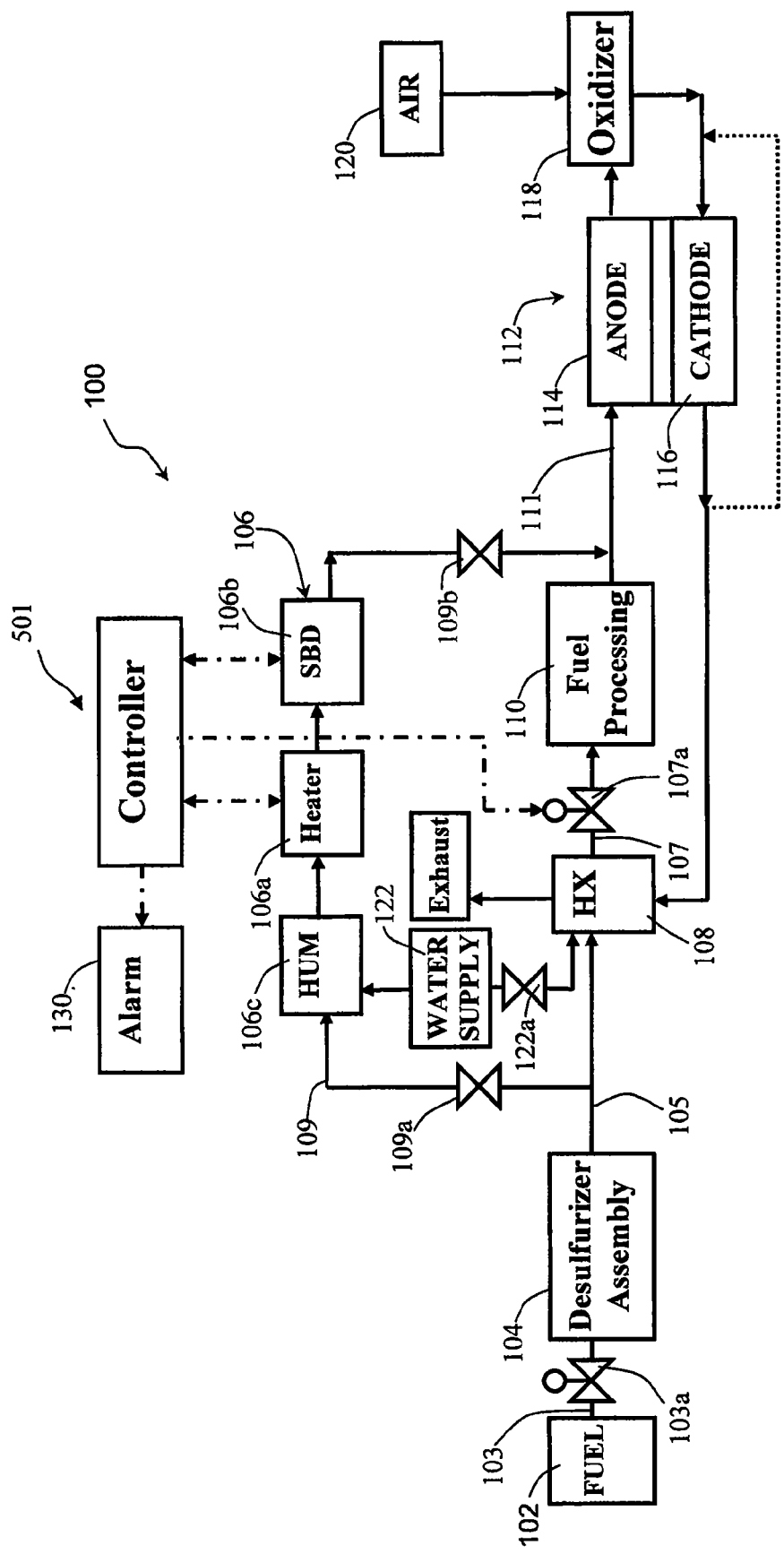
FIG. 5 shows another embodiment of a fuel cell system employing a sulfur breakthrough monitoring assembly for detecting sulfur breakthrough in unhumidified fuel.

FIG. 5 shows an example of the embodiment of the sulfur breakthrough monitoring assembly of FIG. 1 wherein the Fuel Utilization Device 11 is a fuel cell system. The components of the fuel cell system in FIG. 5 which are the same or similar to those of FIG. 2 are labeled using the same reference numbers and detailed description of these components is omitted. As shown in FIG. 5, the sulfur breakthrough monitoring assembly 106 receives a portion of the desulfurized fuel from the desulfurizer assembly 104 directly via the connecting line 109 without being first humidified by the humidifier assembly 108. Also, in FIG. 5, the sulfur breakthrough monitoring assembly 106 includes a humidifier 106c, the heater 106a and the sulfur breakthrough detector 106b. The humidifier 106c of the monitoring assembly 106 receives the fuel conveyed through the connecting line 109 and humidifies the fuel using water from the water supply 122. The humidifier 106c humidifies the fuel so that the steam to carbon ratio (S/C) of the fuel output from the humidifier is between 1.5 and 3. Humidified fuel output from the humidifier 106c is then supplied to the heater 106a, which heats the humidified fuel and outputs the heated humidified fuel to the sulfur breakthrough detector 106b. The configurations of the heater and sulfur breakthrough detector of the monitoring assembly are shown in FIGS. 3A and 3B and described above.

As shown in FIG. 5, the fuel cell system 100 may also include a humidifier 108 downstream of the connecting line 109 for humidifying the desulfurized fuel. In such cases, the humidifier 108 receives the remaining potion of the desulfurized fuel from the desulfurizing assembly 104 via the connecting line 105 and humidifies the fuel using water from the water supply 122. The operation of the sulfur breakthrough monitoring assembly 106, controlled by the controller 501, is described above with respect to FIGS. 3A-4B.

Figure 6:
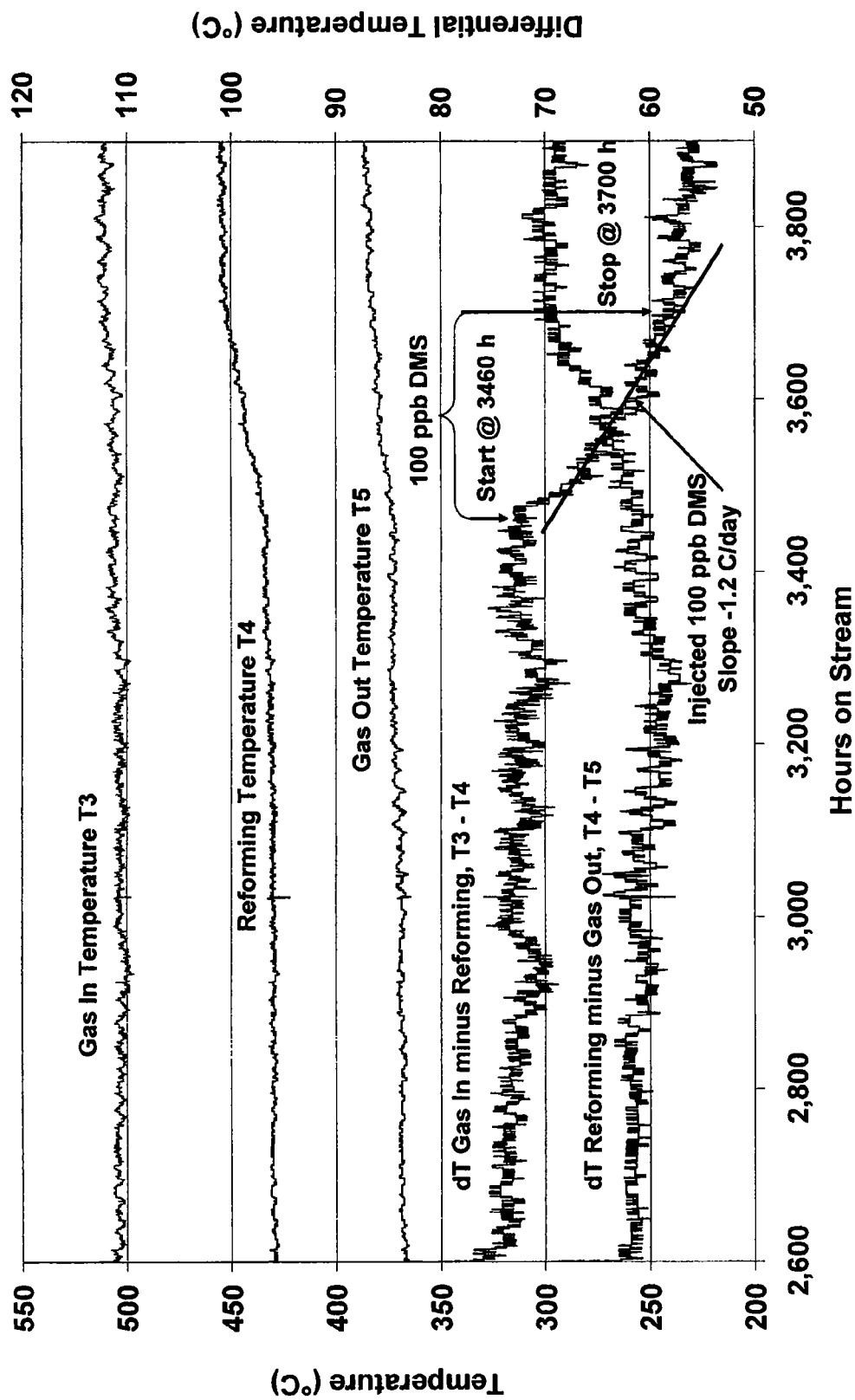
FIGS. 6 through 8 show graphs of temperature measurements in the sulfur breakthrough detection assemblies over time.

The operation of the sulfur breakthrough monitoring assembly 206 as shown in FIG. 3A as operated under the configuration shown in FIG. 1, with fuel and water flow control independent of power plant operation, was tested by conveying humidified natural gas through the monitoring assembly and adding sulfur-containing compounds, such as DMS, to the fuel. FIG. 6 shows a graph of the temperatures and temperature differences in the monitoring assembly. In FIG. 6, the X-axis represent the operating time, by hours on stream, of the sulfur breakthrough monitoring assembly, while the Y-axis represent the temperature (° C.) readings and the temperature difference determinations (dT's in ° C.). As shown in FIG. 6, the temperature measurements of the temperature sensors T3, T4 and T5 in the sulfur breakthrough detector were monitored and recorded as Gas In (T3), Reforming Bed (T4) and Gas Out (T5) for approximately 4,000 hours of operation. The graph in FIG. 6 focuses on the time period of 2,600 to 4,000 hours, highlighting the deliberate poisoning after operating for several hundred hours at a steady state without poisoning. In addition, temperature differences between T3 and T4 and between T4 and T5 were recorded as dT Gas In–Reforming (T3–T4) and as dT Reforming–Gas Out (T4–T5), respectively, so that dT Gas In–Reforming corresponds TDY_FLOAT discussed above. As discussed above, the change in temperature differences between T3 and T4, i.e. dT Gas In–Reforming, is directly related to the reforming process in the catalyst bed and a decrease in dT Gas In–Reforming indicates a reduction in the reforming process, typically due to sulfur poisoning of the reforming catalyst. As also discussed above, the change in the temperature differences between T4 and T5, i.e. dT Reforming–Gas Out, is also related to the flow rate of the fuel through the sulfur breakthrough detector and also to the reforming process in the catalyst bed, so that a significant increase in dT Reforming–Gas Out indicates a low flow rate of the fuel through the sulfur breakthrough detector. In addition, when the dT Reforming–Gas Out increases due to sulfur poisoning of the reforming catalyst bed, the dT Reforming–Gas Out also increases due to greater heat loss in the outlet portion of the sulfur breakthrough detector. As shown in FIG. 6, the dT Reforming–Gas Out and dT Gas In–Reforming were relatively constant, with small variations prior to the addition of the DMS. Starting at 3,460 hours a 100 ppb concentration of DMS was added to the fuel and was stopped at 3,700 hours. During the time when DMS was being added to the fuel, it can be seen that dT Gas In–Reforming dropped from about 73° C. to about 57° C. over the 240 hours, or 10 days, elapsed between 3,460 hours and 3,700 hours. This gives an average temperature drop of 1.6° C. per day, with the drop in dT Gas In–Reforming beginning about ½ day after the addition of DMS was started. In addition, the rate at which dT Gas In–Reforming dropped was the greatest during the first 7 days since the beginning of the drop. Subsequently, a stable decreased rate of about 1.2° C. occurred over several days, as shown on the linear approximation drawn of FIG. 6. Note that this rate is more than double the predicted rate of 0.55° C./day for 100 ppb sulfur poison, indicating higher sensitivity to sulfur in this case. As can also be seen in FIG. 6, while the DMS was being added to the fuel, the dT Reforming–Gas Out increased over about the same time period as the drop in the dT Gas In–Reforming from about 60° C. to about 71° C. The graph of FIG. 6 clearly shows the effect that the addition of a sulfur-containing compound, such as DMS, has on the temperature of the reforming catalyst bed and on the temperature of the fuel being output from the sulfur breakthrough detector.

Figure 7A:
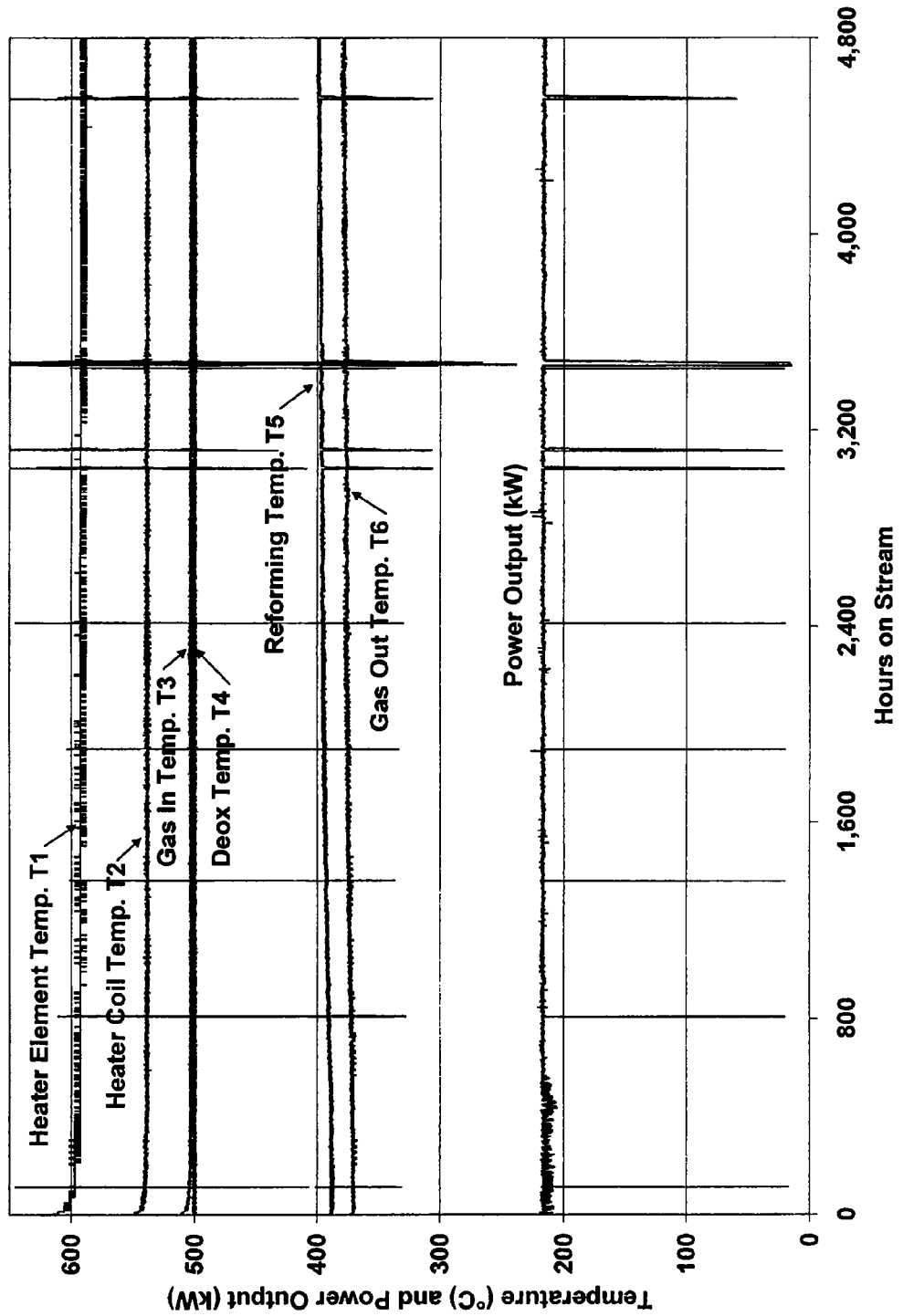
Figure 7B:
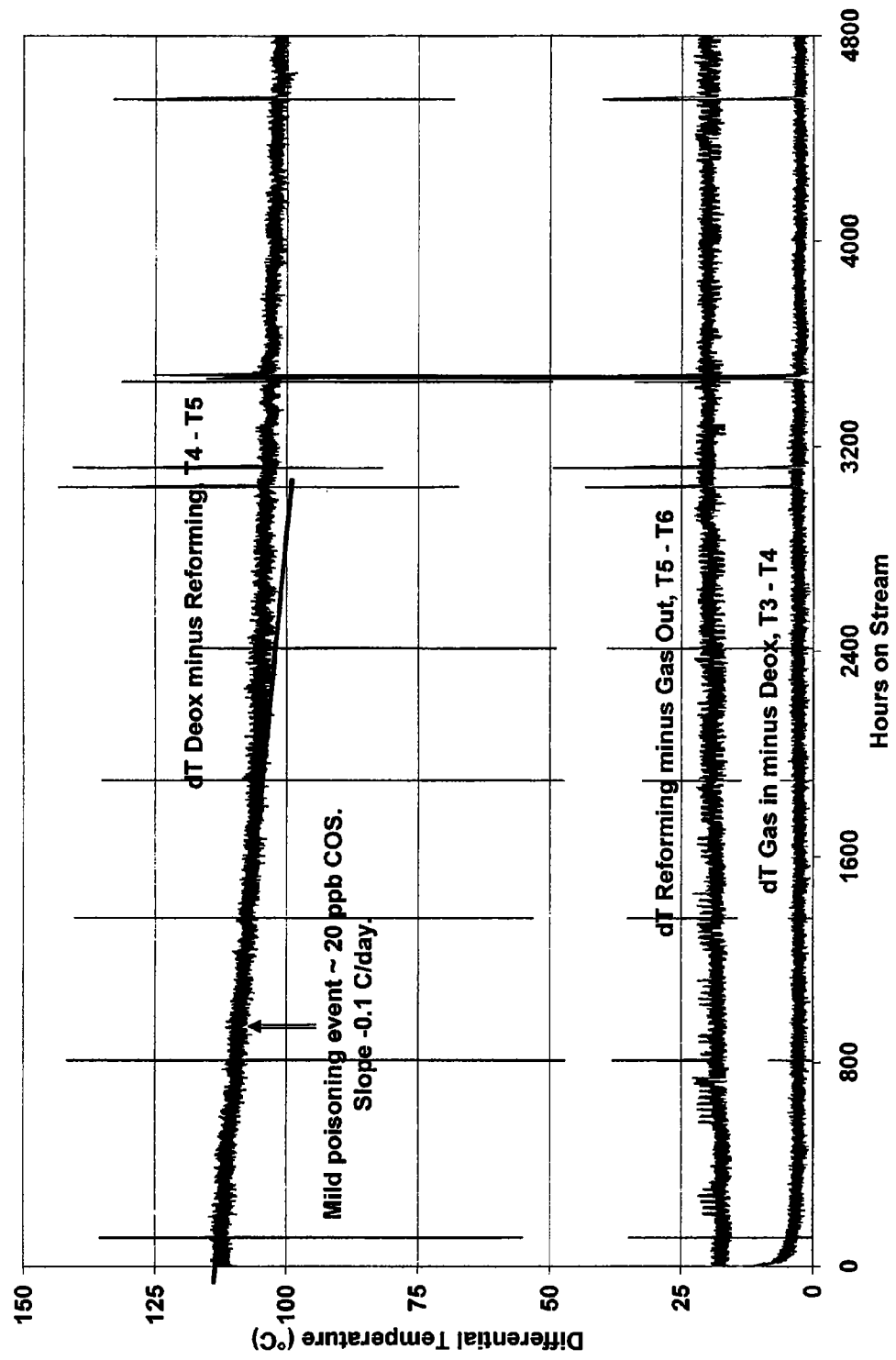

The operation of the sulfur breakthrough monitoring assembly 306 as shown in FIG. 3B and as operated in conjunction with a fuel cell in the configuration of FIG. 2 was also tested. In this configuration the humidified fuel entering the sulfur breakthrough monitoring assembly 306 is dependent on the fuel cell power plant operation. FIGS. 7A and 7B show graphs of the temperatures and temperature differences, respectively, in the monitoring assembly 306. In both FIGS. 7A and 7B, the X-axis represent the operating time, in hours on stream, of the sulfur breakthrough monitoring assembly, while the Y-axis represent the temperature (° C.) readings and the temperature difference determinations (dT's in ° C.). As also shown, the Y-Axis of FIG. 7A also represents the fuel cell power plant output in kilowatts (kW). As shown in FIG. 7A, the temperature measurements of the temperature sensors T1, T2, T3, T4, T5 and T6 in the sulfur breakthrough monitoring assembly 306 were monitored and recorded as Heater Element (T1), Heater Coil (T2), Gas In (T3), Deoxidizer Bed (T4), Reforming Bed (T5) and Gas Out (T6) for the first 4,800 hours of operation. The graph in FIG. 7A demonstrates controlling of the Deoxidizer temperature T4 as required for proper operation of the sulfur breakthrough monitoring assembly. As also shown in FIG. 7A, the fuel cell power plant output is normally steady at 216 kW, with rapid dips to about 20 kW and with rapid recovery to 216 kW occurring roughly once every 600 hours, or about once every 25 days. These fluctuations in the fuel cell power plant output are most frequently caused by disruptions, such as rapid voltage variations, on the power grid which force the fuel cell inverter to separate from the power grid. The graph in FIG. 7A demonstrates that the control strategy used to operate the sulfur breakthrough monitoring assembly is able to accept and recover these transients without ill effects to the detector device of the monitoring assembly.

The graph in FIG. 7B shows the temperature differences between T3 and T4, between T4 and T5 and between T5 and T6 as dT Gas In–Deoxidizer (T3–T4), dT Deoxidizer–Reforming (T4–T5), and dT Reforming–Gas Out (T5–T6), respectively. In FIG. 7B, dT Deoxidizer–Reforming corresponds to TDY_FLOAT, as discussed above. As shown, shortly after the sulfur breakthrough detector was installed, the monitoring assembly 306 started to indicate sulfur breakthrough, as shown by the line drawn through the curve of the dT Deoxidizer–Reforming (T4–T5), which has a slope of –0.1° C./day. Because the sulfur breakthrough detector was registering a mild sulfur breakthrough event, field samples were collected and analyzed by gas chromatography to a sulfur chemiluminescence detector, to quantify sulfur in the fuel samples by species down to 10 ppb. This sampling determined that, in fact, carbonyl sulfide, or COS, was getting through the desulfurization system at about 20 ppb. Testing of the inlet sample determined that the cause of the sulfur breakthrough was a high excursion on the COS concentration of the inlet natural gas. Subsequently, the high inlet COS excursion resolved on its own, and natural gas completely clean of sulfur was entering the fuel cell power plant. As the gas became free of sulfur, the downward slope of dT Deoxidizer–Reforming (T4–T5) recorded in the sulfur breakthrough monitoring assembly leveled off. The graph in FIG. 7B also shows that the flow to the sulfur breakthrough detector device was maintained in the proper range, as determined by both the dT Gas In–Deoxidizer, and dT Reforming–Gas Out, except for the episodes when the power plant power output fluctuated as shown in FIG. 7A, as expected.

The corresponding differential temperatures in FIG. 6 and FIG. 7B are different due to changes in the detector design. What is important, however, is the trending of the differential temperature within any given operation rather than the absolute value or comparing one unit to another.

Figure 8:
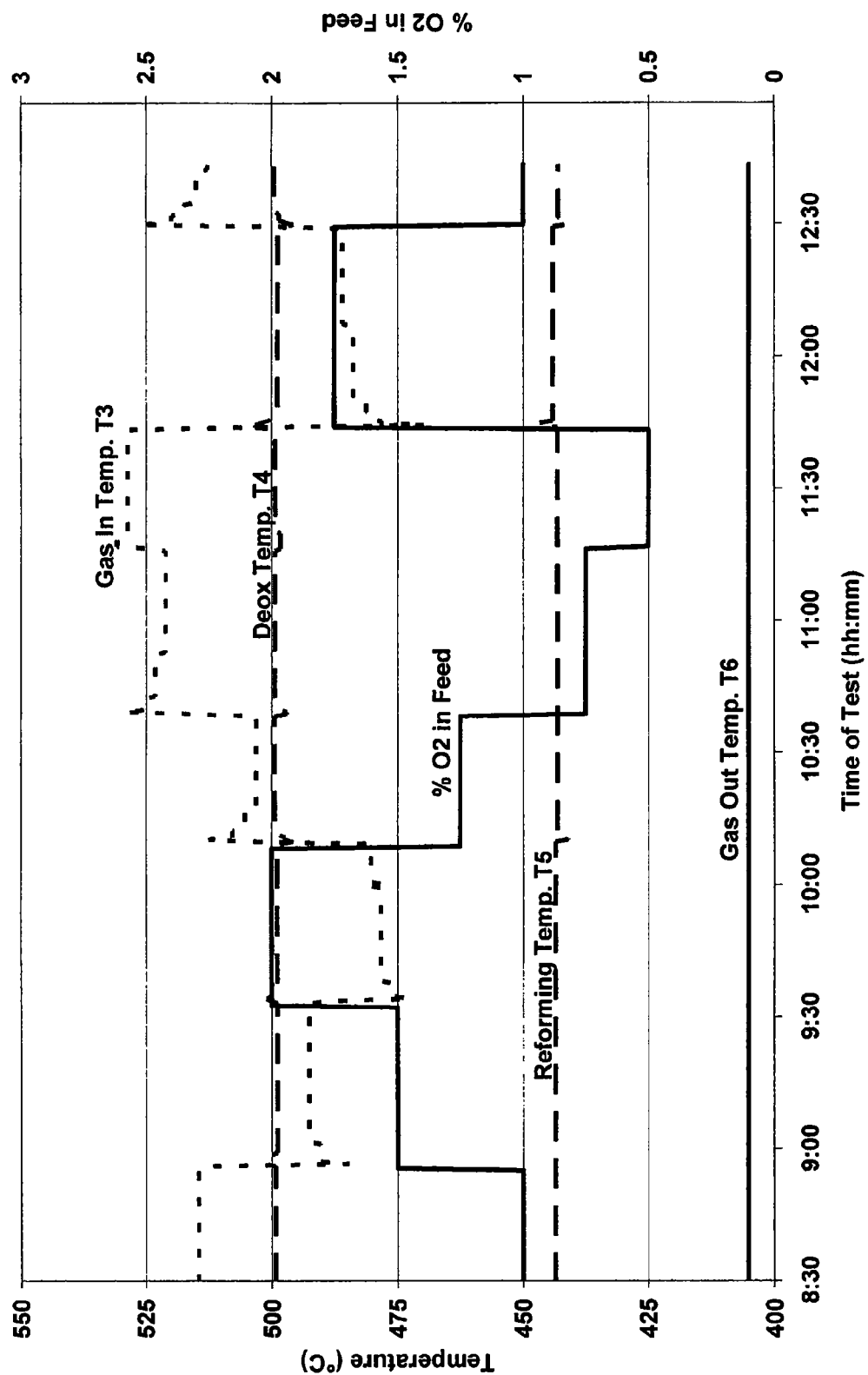

The graph of FIG. 8 shows the temperature variations over time of the sulfur breakthrough monitoring assembly 306 as shown in FIG. 3B and as operated using the configuration shown in FIG. 1, with fuel and water flow control independent of the power plant operation. Specifically, FIG. 8 shows the system response to fluctuation of oxygen content in a simulated anaerobic digester gas (ADG) fuel. As the oxygen level in the feed gas is varied between 0.5% and 2%, the heat generated in the Deoxidizer bed varies, with more heat being released as the oxygen level is increased. However, as discussed above, the Deoxidizer temperature is maintained constant at 500° C. by controlling the heater of the monitoring assembly 306, which in effect adjusts the gas inlet temperature to counteract the variations in the heat generated in the Deoxidizer resulting from the varying oxygen content. The graph of FIG. 8 demonstrates stable control of the Deoxidizer temperature despite the fluctuations of the oxygen content of the fuel supply, as required for stable operation with low level detection sulfur breakthrough. Of equal importance is the demonstration that the Reforming temperature T5 remains constant, indicating complete deoxidization of the fuel prior to entering the reforming bed and that there is no degradation of the reforming bed due to the oxygen content in the feed fuel. For endurance tests, addition systems were operated in the same configuration for over 6 months with 1.0-1.5% oxygen with no apparent loss in activity of the reforming catalyst and no loss of sulfur detection by the sulfur breakthrough monitoring assembly.

The sulfur breakthrough monitoring assembly of the present invention is capable of monitoring for and identifying sulfur breakthrough which either gradually increases in the fuel during operation or which occurs suddenly due to failure of the desulfurizer assembly. As described above, the monitoring assembly of the present invention can be used with multiple types of fuel, including natural gas and ADG, and is capable of sensing the presence of all species of sulfur-containing compounds, thus making the operation of the monitoring assembly sulfur species independent. In addition, the monitoring assembly has a high sensitivity due to the temperature and fuel flow control in the monitoring assembly. The cost of manufacturing of the monitoring assembly of the present assembly is low, and as shown in FIGS. 1 and 2, the monitoring assembly can be easily back-fitted to many existing plants that require sulfur monitoring in the fuel.

In all cases it is understood that the above-described arrangements are merely illustrative of the many possible specific embodiments which represent applications of the present invention. Numerous and varied other arrangements can be readily devised in accordance with the principles of the present invention without departing from the spirit and the scope of the invention.

I claim:

1. A sulfur breakthrough monitoring assembly for use in a fuel utilization system for detecting sulfur-containing compounds in desulfurized fuel, said monitoring assembly comprising:
    a heater for heating desulfurized fuel that has been humidified to a predetermined temperature, said predetermined temperature being between 450° C. and 600° C.;
    a sulfur breakthrough detector adapted to receive heated fuel from said heater and including at least a reforming catalyst bed for reforming said heated fuel and a plurality of temperature sensors including a first temperature sensor for sensing temperature of said heated fuel before said fuel is conveyed through said reforming catalyst bed and a second temperature sensor for sensing temperature in said reforming catalyst bed; and
    a controller programmed to determine whether concentration of said sulfur-containing compounds in the fuel exceeds a first predetermined concentration based on temperature outputs from said first and second temperature sensors,
    wherein the controller receives temperature outputs from said first and second temperature sensors, and is programmed to:
    determine a plurality of differences between temperature outputs of said first and second temperature sensors over predetermined time,
    determine, based on the determined plurality of differences between temperature outputs of the first and second temperature sensors, a rate at which the difference between outputs of the first and second temperature sensors changes; and
    determine that concentration of said sulfur-containing compounds in said fuel exceeds the first predetermined concentration if the determined rate is equal to or greater than a first predetermined rate.

2. A sulfur breakthrough monitoring assembly in accordance with claim 1, wherein the sulfur breakthrough monitoring assembly is adapted to receive water from a water supply and the heater heats the desulfurized fuel and water to the predetermined temperature, said sulfur breakthrough monitoring assembly including:
    a water flow controller for controlling the flow of water to the sulfur breakthrough monitoring assembly; and
    a fuel flow controller for controlling the flow of the desulfurized fuel to the sulfur breakthrough monitoring assembly.

3. A sulfur breakthrough monitoring assembly in accordance with claim 2, wherein the sulfur breakthrough detector includes a housing having a cylindrical shape with a height of the housing being 3 times the diameter of the housing and the reforming catalyst bed is supported within the housing at a predetermined distance away from an outlet of the housing and has a predetermined thickness, and
    wherein said fuel flow controller and the water flow controller control the flow of fuel and water so as to provide humidified fuel with a S/C ratio of 1.3 to 3.0 to said sulfur breakthrough detector and said controller controls the flow of said humidified fuel so that the space velocity of said humidified fuel through said reforming catalyst bed is between 30,000/hr and 120,000/hr and superficial velocity of said humidified fuel through said reforming catalyst bed is between 7 and 60 cm/sec.

4. A sulfur breakthrough monitoring assembly in accordance with claim 3, wherein:
    said sulfur breakthrough detector further comprises a third temperature sensor for sensing temperature of the humidified fuel after the humidified fuel is conveyed through said reforming catalyst bed, and
    said controller receives temperature outputs from said second and third temperature sensors, determines whether the said humidified fuel flow through said sulfur breakthrough detector is sufficiently high and stable by determining whether the difference between said temperature outputs from said second and third temperature sensors is smaller than a first predetermined amount and whether said difference between said temperature outputs from said second and third temperature sensors varies by more than a second predetermined amount,
    wherein said controller determines whether concentration of said sulfur-containing compounds in the fuel exceeds the first predetermined concentration only if the controller determines that the difference between the temperature outputs from the second and third temperature sensors is smaller than the first predetermined amount and that the difference between the temperature outputs from the second and third temperature sensors does not vary by more than the second predetermined amount.

5. A sulfur breakthrough monitoring assembly in accordance with claim 3, wherein said first predetermined amount is 80° C. and said second predetermined amount is 4° C./hour.

6. A sulfur breakthrough monitoring assembly in accordance with claim 1, wherein the sulfur breakthrough monitoring assembly receives humidified desulfurized fuel and the heater heats the humidified desulfurized fuel to the predetermined temperature.

7. A sulfur breakthrough monitoring assembly in accordance with claim 1, wherein said first predetermined concentration of said sulfur-containing compounds is 200 ppb and said first predetermined rate is 1.1° C. per day.

8. A sulfur breakthrough monitoring assembly in accordance with claim 1, wherein when said controller determines that the concentration of said sulfur-containing compounds in the fuel exceeds said first predetermined concentration, said controller performs one or more of (1) activates an alarm, and (2) controls said fuel utilization system to perform one or more actions.

9. A sulfur breakthrough monitoring assembly in accordance with claim 8, wherein said one or more predetermined actions include one or more of: controlling the flow of fuel to one or more components of said fuel utilization system to reduce or inhibit said fuel flow, controlling the flow of fuel to said fuel utilization system to reduce or inhibit said fuel flow, controlling a desulfurizer assembly of said fuel utilization system to redirect the flow of fuel to be desulfurized from an operating desulfurizer to another desulfurizer of said desulfurizer assembly, controlling said desulfurizer assembly of said fuel utilization system to regenerate or replace the operating desulfurizer, and controlling a said fuel utilization system to switch from an operating fuel supply to another fuel supply.

10. A sulfur breakthrough monitoring assembly in accordance with claim 8, wherein:
    if said controller determines that the concentration of said sulfur-containing compounds in the fuel exceeds said first predetermined concentration based on temperature outputs from said first and second temperature sensors, said controller determines whether the concentration of said sulfur-containing compounds in the fuel exceeds a second predetermined concentration, greater than said first predetermined concentration, based on whether the determined rate at which the difference between temperature outputs from said first and second temperature sensors changes is equal to or greater than a second predetermined rate, the second predetermined rate being greater than said first predetermined rate, and if said controller determines that said concentration of said sulfur containing compounds in the fuel exceeds said second predetermined concentration, said controller activates an escalated alarm and performs one or more predetermined escalated actions, said predetermined escalated actions including one or more of: controlling the flow of fuel to one or more components of said fuel utilization system to inhibit said fuel flow, controlling the flow of fuel to said fuel utilization system to inhibit said fuel flow and ceasing operation of said fuel utilization system.

11. A sulfur breakthrough monitoring assembly in accordance with claim 10, wherein said second predetermined concentration is 800 ppb and said second predetermined rate is 4.4° C. per day.

12. A sulfur breakthrough monitoring assembly in accordance with claim 1, wherein:
said sulfur breakthrough detector further comprises a deoxidizing catalyst bed disposed in series with said reforming catalyst bed so that the fuel is first conveyed through said deoxidizing catalyst bed and thereafter through said reforming catalyst bed, and
said first temperature sensor senses temperature of said fuel in said deoxidizing catalyst bed.

13. A sulfur breakthrough monitoring assembly, in accordance with claim 1, wherein:
said heater includes at least one temperature sensor; and
said controller includes:
a first temperature controller for receiving a temperature output from said at least one temperature sensor in said heater and outputting a first control variable output,
a second temperature controller for receiving a temperature output from said first temperature sensor and outputting a second control variable output, and
a low selector for receiving said first and second control variable outputs and selecting a lower one of said first and second control variable outputs,
said controller controlling the heating of said heater based on the selected lower one of said first and second control variable outputs.

14. A sulfur breakthrough monitoring assembly in accordance with claim 1, wherein said fuel utilization system is a fuel cell system.

15. A sulfur breakthrough monitoring assembly for use in a fuel utilization system for detecting sulfur-containing compounds in fuel, said monitoring assembly comprising:
a heater for heating fuel to a predetermined temperature;
a sulfur breakthrough detector adapted to receive heated fuel from said heater and including a housing, a reforming catalyst bed for reforming said heated fuel disposed in the housing and a plurality of temperature sensors including a first temperature sensor for sensing temperature of said heated fuel before said fuel is conveyed through said reforming catalyst bed and a second temperature sensor for sensing temperature in said reforming catalyst bed, wherein the housing has a cylindrical shape with a height of the housing being 3 times the diameter of the housing and the reforming catalyst bed has a predetermined thickness and is supported within the housing at a predetermined distance away from an outlet of the housing; and
a controller programmed to determine whether concentration of said sulfur-containing compounds in the fuel exceeds a first predetermined concentration based on differences in temperature outputs from said first and second temperature sensors, and programmed to control the flow of fuel through said sulfur breakthrough detector,
wherein the predetermined thickness of the reforming catalyst bed disposed in the housing is such that space velocity of said fuel through said reforming catalyst bed is between 30,000/hr and 120,000/hr when superficial velocity of said fuel through said reforming catalyst bed is between 7 and 60 cm/sec.

16. A sulfur breakthrough monitoring assembly in accordance with claim 15, wherein the sulfur breakthrough monitoring assembly is adapted to receive water from a water supply and the heater heats the desulfurized fuel and water to the predetermined temperature, said sulfur breakthrough monitoring assembly including:
a water flow controller for controlling the flow of water to the sulfur breakthrough monitoring assembly; and
a fuel flow controller for controlling the flow of the desulfurized fuel to the sulfur breakthrough monitoring assembly.

17. A sulfur breakthrough monitoring assembly in accordance with claim 15, wherein the sulfur breakthrough monitoring assembly receives humidified desulfurized fuel and the heater heats the humidified desulfurized fuel to the predetermined temperature.

18. A sulfur breakthrough monitoring assembly in accordance with claim 15, wherein said space velocity of said fuel is 90,000/hr and said superficial velocity is 25 cm/sec.

19. A sulfur breakthrough assembly in accordance with claim 18, wherein:
said sulfur breakthrough detector further comprises a third temperature sensor for sensing temperature of the fuel after the fuel is conveyed through said reforming catalyst bed, and
said controller receives temperature outputs from said second and third temperature sensors, and determines whether the difference between said temperature outputs from said second and third temperature sensors exceeds a first predetermined amount and whether said difference between said temperature outputs from said second and third temperature sensors is less than a second predetermined amount.

20. A sulfur breakthrough assembly in accordance with claim 15, wherein:
said sulfur breakthrough detector further comprises a deoxidizing catalyst bed disposed in series with said reforming catalyst bed so that the fuel is first conveyed through said deoxidizing catalyst bed and thereafter through said reforming catalyst bed, and
said first temperature sensor senses temperature of said fuel in said deoxidizing catalyst bed.

21. A method of detecting sulfur-containing compounds in desulfurized fuel for use in a fuel utilization system, comprising the steps of:
heating desulfurized fuel to a predetermined temperature using a heater, said predetermined temperature is between 450° C. and 600° C.;
receiving fuel heated in said heating step in a reforming catalyst bed and reforming said heated fuel in a reforming catalyst bed;

first sensing step of sensing a first temperature of said heated fuel prior to said fuel being received in said reforming catalyst bed;

second sensing step of sensing a second temperature in said reforming catalyst bed;

determining whether concentration of said sulfur-containing compounds in the fuel exceeds a first predetermined concentration based on said first and second temperatures sensed in said first and second sensing steps, wherein the determining comprises:

determining a plurality of differences between the first and second temperatures sensed in the first and second sensing steps over predetermined time, determining, based on the determined plurality of differences between temperature outputs of the first and second temperature sensors, a rate at which the difference between outputs of the first and second temperature sensors changes, and determining that concentration of the sulfur-containing compounds in the fuel exceeds the first predetermined concentration if the determined rate is equal to or greater than a first predetermined rate.

22. A method of detecting sulfur-containing compounds in accordance with claim 21, further comprising:

providing water to the sulfur breakthrough monitoring assembly from a water supply;

controlling the flow of water to the sulfur-breakthrough monitoring assembly; and controlling the flow of desulfurized fuel to the sulfur breakthrough monitoring assembly;

wherein the heating step comprises heating the desulfurized fuel and water to the predetermined temperature to form heated humidified fuel.

23. A method of detecting sulfur-containing compounds in accordance with claim 22, wherein the reforming catalyst bed is disposed in a housing having a cylindrical shape with a height of the housing being 3 times the diameter of the housing and the reforming catalyst bed is supported within the housing at a predetermined distance away from an outlet of the housing and has a predetermined thickness, and the method further comprising controlling the flow of humidified fuel through said reforming catalyst bed so that space velocity of said fuel through the reforming catalyst bed is between 30,000/hr and 120,000/hr and superficial velocity of the fuel through the reforming catalyst bed is between 7 and 60 cm/sec.

24. A method of detecting sulfur-containing compounds in accordance with claim 23, further comprising:

a third step of sensing temperature of the fuel after the fuel is conveyed through said reforming catalyst bed;

a second determining step of determining whether the flow of said humidified fuel through said sulfur breakthrough detector is sufficiently high and stable by determining whether the difference between said temperatures sensed in the second and third sensing steps is smaller than a first predetermined amount and whether said difference between the temperatures sensed in said second and third sensing steps does not vary more than a second predetermined amount, and wherein, said determining step determines whether concentration of said sulfur-containing compounds in the fuel exceeds the first predetermined concentration only if said second determining step determines that the difference between the temperatures sensed in said second and third sensing steps is smaller than the first predetermined amount and that the difference between temperature sensed in said second and third sensing steps does not vary by more than the second predetermined amount.

25. A method of detecting sulfur-containing compounds in accordance with claim 21, wherein the heating step comprises heating humidified desulfurized fuel to the predetermined temperature to form heated humidified fuel.

26. A method of detecting sulfur-containing compounds in accordance with claim 21, further comprising at least one of:

activating an alarm when said determining step determines that the concentration of said sulfur-containing compounds in the fuel exceeds the first predetermined concentration; and controlling the fuel utilization system to perform one or more actions when said determining step determines that the concentration of the sulfur-containing compounds in the fuel exceeds the first predetermined concentration, said one or more predetermined actions including one or more of: controlling the flow of fuel to one or more components of said fuel utilization system to reduce or inhibit said fuel flow, controlling the flow of fuel to said fuel utilization system to reduce or inhibit said fuel flow, controlling a desulfurizer assembly of said fuel utilization system to redirect the flow of fuel to be desulfurized from an operating desulfurizer to another desulfurizer of said desulfurizer assembly, controlling said desulfurizer assembly of said fuel utilization system to regenerate or replace the operating desulfurizer, and controlling a said fuel utilization system to switch from an operating fuel supply to another fuel supply.

27. A method of detecting sulfur-containing compounds in accordance with claim 21, wherein:

said determining step further comprises determining whether the concentration of sulfur-containing compounds in the fuel exceeds a second predetermined concentration greater than the first predetermined concentration based on whether the determined rate at which the difference between said first and second temperatures changes is equal to or greater than a second predetermined rate, the second predetermined rate being greater than said first predetermined rate, when the determining step determines that the concentration of said sulfur-containing compounds in the fuel exceeds the first predetermined concentration; and activating an escalated alarm and performing one or more escalated actions, if said determining step determines that the concentration of the sulfur-containing compounds in the fuel exceeds the second predetermined concentration, said predetermined escalated actions including one or more of: controlling the flow of fuel to one or more components of said fuel utilization system to inhibit said fuel flow, controlling the flow of fuel to the fuel utilization system to inhibit said fuel flow, and halting operation of said fuel utilization system.

28. A method of detecting sulfur-containing compounds in accordance with claim 27, wherein said first predetermined concentration is 200 ppb and said first predetermined rate is 1.1° C. per day, and said second predetermined concentration is 800 ppb and said second predetermined rate is 4.4° C. per day.

29. A method of detecting sulfur-containing compounds in accordance with claim 21, further comprising:

deoxidizing said heated desulfurized fuel in a deoxidizing catalyst bed disposed in series with said reforming catalyst bed so that said heated desulfurized fuel is first conveyed through said deoxidizing catalyst bed and thereafter through said reforming catalyst bed, wherein said first sensing step senses the temperature of the fuel in the deoxidizing catalyst bed.

30. A method of detecting sulfur-containing compounds in accordance with claim 21, further comprising:

a fourth sensing step of sensing a temperature in said heater;

receiving the temperature sensed in said fourth sensing step in a first temperature controller and outputting a first control variable output;

receiving the temperature sensed in the first sensing steps and outputting a second control variable output;

selecting a lower one of said first and second control variable outputs; and controlling the heating by said heater based on the selected lower one of said first and second control variable outputs.

* * * * *